(12) United States Patent
Sandler

(10) Patent No.: US 11,104,738 B2
(45) Date of Patent: Aug. 31, 2021

(54) MONOCLONAL ANTIBODIES TO HUMAN FLT3/FLK2 RECEPTOR PROTEIN

(71) Applicant: HEMOGENYX PHARMACEUTICALS LLC, Brooklyn, NY (US)

(72) Inventor: Vladislav Sandler, New York, NY (US)

(73) Assignee: HEMOGENYX PHARMACEUTICALS LLC, Brooklyn, NY (US)

( * ) Notice: Subject to any disclaimer, the term of this patent is extended or adjusted under 35 U.S.C. 154(b) by 294 days.

(21) Appl. No.: 16/506,764

(22) Filed: Jul. 9, 2019

(65) Prior Publication Data
US 2019/0389955 A1 Dec. 26, 2019

Related U.S. Application Data

(63) Continuation-in-part of application No. 16/091,139, filed as application No. PCT/US2017/025951 on Apr. 4, 2017, now Pat. No. 11,021,536.

(60) Provisional application No. 62/317,906, filed on Apr. 4, 2016.

(51) Int. Cl.
| | |
|---|---|
| C07K 16/28 | (2006.01) |
| A61K 39/395 | (2006.01) |
| C07K 14/705 | (2006.01) |
| C07K 14/71 | (2006.01) |
| A61K 39/00 | (2006.01) |

(52) U.S. Cl.
CPC ...... *C07K 16/2863* (2013.01); *A61K 39/3955* (2013.01); *A61K 2039/505* (2013.01); *C07K 2317/33* (2013.01); *C07K 2317/56* (2013.01); *C07K 2317/565* (2013.01); *C07K 2317/76* (2013.01); *C07K 2317/77* (2013.01); *C07K 2317/92* (2013.01)

(58) Field of Classification Search
CPC .......... A61K 2039/505; A61K 39/3955; A61K 39/39558; C07K 16/2863; C07K 16/28; C07K 16/2896; C07K 2317/565; C07K 2317/56; C07K 2317/77; C07K 14/71
See application file for complete search history.

(56) References Cited

U.S. PATENT DOCUMENTS

| | | | |
|---|---|---|---|
| 6,054,297 | A | 4/2000 | Carter et al. |
| 9,023,996 | B2 | 5/2015 | Grosse-Hovest et al. |
| 2012/0328612 | A1 | 12/2012 | Grosse-Hovest et al. |
| 2015/0119555 | A1 | 4/2015 | Jung et al. |
| 2018/0002435 | A1 | 1/2018 | Sasu et al. |
| 2019/0127464 | A1 | 5/2019 | Sandler |

FOREIGN PATENT DOCUMENTS

| | | |
|---|---|---|
| WO | 2016/023909 A1 | 2/2016 |
| WO | 2017176760 A3 | 11/2017 |
| WO | 2018193231 A1 | 10/2018 |

OTHER PUBLICATIONS

Akashi K, et al. A clonogenic common myeloid progenitor that gives rise to all myeloid lineages. Nature. Mar. 3, 2000;404(6774):193-7.
Alberts, B., et al. The adaptive immune system. Molecular Biology of the Cell, Chapter 24, Garland Science, NY, 2002.
Battaglia, M. et al., "Rapamycin promotes expansion of functional CD4+CD25+Foxp3+ regulator T cells of both healthy subjects and type 1 diabetic patients," J. Immunol., 177: 8338-8347 (2006).
Bonnet D et al., Human acute myeloid leukemia is organized as a hierarchy that originates from a primitive hematopoietic cell. Nat Med. 1997; 3: 730-737.
Bydlowski, Sergio Paulo and De Lara Janz, Felipe. (2012). Hematopoietic Stem Cell in Acute Myeloid Leukemia Development, Advances in Hematopoietic Stem Cell Research, Dr. Rosana Pelayo (Ed.), ISBN: 978-953-307-930-1.
Carbone A et al., Expression Status of BCL-6 and Syndecan-1 Identifies Distinct Histogenetic Subtypes of Hodgkin's Disease. Blood. 1998; 92: 2220-2228.
Delogu A, et al. Gene repression by Pax5 in B cells is essential for blood cell homeostasis and is reversed in plasma cells. Immunity. Mar. 2006;24(3):269-81.
Desai-Mehta, A. et al., "Hyperexpression of CD40 ligand by B and T cells in human lupus and its role in pathogenic autoantibody production," J. Clin. Invest., 97(9): 2063-2073 (1996).
Durben, M., et al. Characterization of a Bispecific FLT3 X CD3 Antibody in an Improved, Recombinant Format for the Treatment of Leukemia. Molecular Therapy, vol. 23, No. 4, 648-655 Apr. 2015.
Fearon DT et al., Arrested Differentiation, the Self-Renewing Memory Lymphocyte, and Vaccination. Science. 2001; 293: 248-250.
Frankfurt O et al., Molecular characterization of acute myeloid leukemia and its impact on treatment. Current Opinion in Oncology (2007) 19(6): 635-649.
Gilliland, DG and Tallman MS, Focus on acute leukemias. Cancer Cell (2002) 1(5): 417-420.
Gordon, M. Stem cells and haemopoiesis. Postgraduate Haematology. Hoffbrand, V., Catovsky, D., Tuddenham, E.G., 5th ed. Blackwell Publishing, (2005) pp. 1-12.
Hamburger AW and Salmon SE. Primary bioassay of human tumor stem cells. Science. 1977; 197: 461-463.
Havens, AM, et al. Blood-Bone Axis and Bone Marrow Microenvironment. In: Bone and Cancer. Topics in Bone Biology. Bronner, F. and Carson, M C.,eds. Springer 2009; vol. 5: pp. 2-4.
Hope KJ et al., Human acute myeloid leukemia stem cells. Archives of Medical Research (2003) 34(6): 507-514.

(Continued)

*Primary Examiner* — Bridget E Bunner
(74) *Attorney, Agent, or Firm* — McCarter & English, LLP; Beverly W. Lubit

(57) ABSTRACT

The described invention provides compositions containing bi-specific antibodies that bind to human tyrosine kinase receptor FLT3/FLK2 receptor protein and to CD3 receptor protein expressed on T-cells and use of the compositions containing the bispecific antibodies in the preparation of a medicament for eliminating hematopoietic stem cells/hematopoietic progenitors (HSC/HP) in a patient.

25 Claims, 10 Drawing Sheets
Specification includes a Sequence Listing.

(56) References Cited

OTHER PUBLICATIONS

Iwaskaki, H. and Akashi, K. "Myeloid lineage commitment from the hematopoietic stem cell," Immunity 26(6) Jun. 2007, 726-40.
Janeway, CA, Jr., The priming of helper T cells, Semin. Immunol. 1(1): 13-20 (1989).
Jones RJ and Armstrong SA, Cancer Stem Cells in Hematopoietic Malignancies. Biol Blood Marrow Transplant. Jan. 2008; 14 (Supplement 1): 12-16.
Jones RJ et al., Cancer Stem Cells: Are We Missing the Target?. J Natl Cancer Inst. 2004; 96: 583-585.
Jones RJ et al., Clonotypic B Cells Circulate in Hodgkin's Lymphoma (HL). Blood. 2006; 108: 470.
Kondo M, et al. Biology of hematopoietic stem cells and progenitors: implications for clinical application. Ann. Rev Immunol. 2003;21:759-806.
Kondo M, et al. Cell-fate conversion of lymphoid-committed progenitors by instructive actions of cytokines. Nature. Sep. 21, 2000;407(6802):383-6.
Kondo, M. "Lymphoid and myeloid lineage commitment in multipotent hematopoietic progenitors," Immunol. Rev. Nov. 2010; 238(1): 37-46.
Konopleva, MY, and Jordan, CT, Leukemia Stem Cells and Microenvironment: Biology and Therapeutic Targeting. J. Clin. Oncol. (2011) 29(5): 591-599.
Kronenberg, M. et al., "Regulation of immunity by self-reactive T cells," Nature 435: 598-604 (2005).
Kukreja A et al., Enhancement of clonogenicity of human multiple myeloma by dendritic cells. J Exp Med. 2006; 203: 1859-1865.
Lane, SW, et al. Differential niche and Wnt requirements during acute myeloid leukemia progression. 2011. Blood 118:2849-2856.
Lapidot T et al., A cell initiating human acute myeloid leukaemia after transplantation into SCID mice. Nature. 1994; 367: 645-648.
Luckey CJ et al., Memory T and memory B cells share a transcriptional program of self-renewal with long-term hematopoietic stem cells. Proc Natl Acad Sci U S A. 2006; 103: 3304-3309.
Manz MG, et al. Dendritic cell potentials of early lymphoid and myeloid progenitors. Blood. Jun. 1, 2001;97 (11):3333-41.
Matsui WH et al., Characterization of clonogenic multiple myeloma cells. Blood. 2004; 103: 2332-2336.
Newcom SR et al., L-428 reed-stemberg cells and mononuclear hodgkin's cells arise from a single cloned mononuclear cell. Int J Cell Cloning. 1988; 6: 417-431.
Pandolfi PP. In vivo analysis of the molecular genetics of acute promyelocytic leukemia. Oncogene (2001) 20(40): 5726-5735.
Park CH et al., Mouse Myeloma Tumor Stem Cells: A Primary Cell Culture Assay. J Natl Cancer Inst. 1971; 46: 411-422.
Paul, W. E., "Chapter 1: The immune system: an introduction," Fundamental Immunology, 4th Edition, Ed. Paul, W. E, Lippicott-Raven Publishers, Philadelphia (1999).
Pollyea DA et al., Acute myeloid leukaemia in the elderly: a review. British Journal of Haematology (2011) 152(5): 523-542.
Rossi, L. et al., Hematopoietic Stem Cell Characterization and Isolation. Methods in Molecular Biology (2011) 750(2): 47-59.
Schwartz, R. H., "T cell anergy," Annu. Rev. Immunol., 21: 305-334 (2003).
Taams, L. S. et al., "Human anergic/suppressive CD4+CD25+ T cells: a highly differentiated and apoptosis-prone population," Eur. J. Immunol., 31: 1122-1131 (2001).
Tenen DG, Disruption of differentiation in human cancer: AML shows the way. Nature Reviews of Cancer (2003) 3(2): 89-101.
Testa U. Leukemia stem cells. Annals of Hematology (2011) 90(3): 245-271.
Traver D, et al. Development of CD8alpha-positive dendritic cells from a common myeloid progenitor. Science (New York, NY. Dec. 15, 2000;290(5499):2152-4.
Warner, JK et al, Concepts of human leukemic development. Oncogene (2004) 23(43): 7164-7177.
Weissman IL. Translating stem and progenitor cell biology to the clinic: barriers and opportunities. Science (New York, NY. Feb. 25, 2000;287(5457):1442-6.
Czechowicz, A. et al. Efficient Transplantation via Antibody-Based Clearance of Hematopoietic Stem Cell Niches. Science 318, 1296 (2007); DOI:10.1126/science.1149726.

| SAMPLES | MFI (IgC FITC) | % POSITIVE CELLS |
|---|---|---|
| UNSTAINED CELLS (GREY) | 1292 | |
| SECONDARY Ab ALONE (RED) | 6905 | 0.78% |
| ISOTYPE CTR (YELLOW) | 13307 | 12% |
| POSITIVE (ANTI-Flt3 Ab) ctr (GREEN) | 26674 | 82% |
| 1-18B SUPE | 14719 | 58% |
| 1-23D SUPE | 13276 | 49% |
| 2-81 SUPE | 11044 | 30% |
| 3-16H SUPE | 15169 | 57% |
| 3-30 SUPE | 13044 | 48% |
| 4-10C SUPE | 10513 | 28% |
| 5-11E SUPE | 10099 | 25% |
| 5-15D SUPE | 12189 | 41% |

| SAMPLE NAME | MFI |
|---|---|
| ISOTYPE CONTROL | 11518 |
| Ab 1-18B | 155105 |
| Ab 1-23 | 119338 |
| Ab 2-81 | 127532 |
| Ab 3-16H | 205877 |
| Ab 3-30 | 150828 |
| Ab 4-10C | 155648 |
| Ab 5-15D | 132994 |
| Ab 5-11E | 124015 |
| SP2/0 wt ON Ab 1-18B | 9722 |
| ANTI-CD 135 | 75775 |
| UNSTAINED SP2/0 CLONE 3 | 6063 |
| SECONDARY Ab | 9522 |

SEQUENCE LISTING

```
<160> NUMBER OF SEQ ID NOS: 28

<210> SEQ ID NO 1
<211> LENGTH: 613
<212> TYPE: PRT
<213> ORGANISM: Homo sapiens

<400> SEQUENCE: 1

Met Glu Trp Ser Trp Val Phe Leu Phe Phe Leu Ser Val Thr Thr Gly
1               5                   10                  15
```

```
Val His Ser Gln Val Gln Leu Gln Gln Pro Gly Ala Glu Leu Val Lys
            20                  25                  30

Pro Gly Ala Ser Leu Lys Leu Ser Cys Lys Ser Gly Tyr Thr Phe
        35                  40                  45

Thr Ser Tyr Trp Met His Trp Val Arg Gln Arg Pro Gly His Gly Leu
 50                  55                  60

Glu Trp Ile Gly Glu Ile Asp Pro Ser Asp Ser Tyr Lys Asp Tyr Asn
 65                  70                  75                  80

Gln Lys Phe Lys Asp Lys Ala Thr Leu Thr Val Asp Arg Ser Ser Asn
             85                  90                  95

Thr Ala Tyr Met His Leu Ser Ser Leu Thr Ser Asp Asp Ser Ala Val
            100                 105                 110

Tyr Tyr Cys Ala Arg Ala Ile Thr Thr Thr Pro Phe Asp Phe Trp Gly
            115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
            210                 215                 220

Lys Pro Ser Asn Thr Lys Val Asp Lys Val Glu Pro Lys Ser Cys
225                 230                 235                 240

Asp Lys Thr His Thr Ser Pro Pro Ser Pro Ala Pro Pro Val Ala Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Gly Val Ser His Glu
            275                 280                 285

Asp Pro Glu Val Lys Phe Asn Trp Tyr Val Asp Gly Val Glu Val His
            290                 295                 300

Asn Ala Lys Thr Lys Pro Arg Glu Glu Gln Tyr Gln Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Gln Leu Pro Ser Pro Ile Glu
            340                 345                 350

Lys Thr Ile Ser Lys Ala Lys Gly Gly Gly Ala Gly Gly Gly Gly
            355                 360                 365

Glu Val Gln Leu Val Glu Ser Gly Gly Leu Val Gln Pro Gly Gly
            370                 375                 380

Ser Leu Arg Leu Ser Cys Ala Ala Ser Gly Tyr Ser Phe Thr Gly Tyr
385                 390                 395                 400

Thr Met Asn Trp Val Arg Gln Ala Pro Gly Lys Gly Leu Glu Trp Val
                405                 410                 415

Ala Leu Ile Asn Pro Tyr Lys Gly Val Thr Thr Tyr Ala Asp Ser Val
            420                 425                 430
```

-continued

```
Lys Gly Arg Phe Thr Ile Ser Val Asp Lys Ser Lys Asn Thr Ala Tyr
            435                 440                 445

Leu Gln Met Asn Ser Leu Arg Ala Glu Asp Thr Ala Val Tyr Tyr Cys
450                 455                 460

Ala Arg Ser Gly Tyr Tyr Gly Asp Ser Asp Trp Tyr Phe Asp Val Trp
465                 470                 475                 480

Gly Gln Gly Thr Leu Val Thr Val Ser Gly Gly Gly Ser Gly
                    485                 490                 495

Gly Gly Gly Ser Gly Gly Gly Ser Asp Ile Gln Met Thr Gln Ser
                500                 505                 510

Pro Ser Ser Leu Ser Ala Ser Val Gly Asp Arg Val Thr Ile Thr Cys
            515                 520                 525

Arg Ala Ser Gln Asp Ile Arg Asn Tyr Leu Asn Trp Tyr Gln Gln Lys
            530                 535                 540

Pro Gly Lys Ala Pro Lys Leu Leu Ile Tyr Tyr Thr Ser Arg Leu Glu
545                 550                 555                 560

Ser Gly Val Pro Ser Arg Phe Ser Gly Ser Gly Ser Gly Thr Asp Tyr
                    565                 570                 575

Thr Leu Thr Ile Ser Ser Leu Gln Pro Glu Asp Phe Ala Thr Tyr Tyr
                580                 585                 590

Cys Gln Gln Gly Asn Thr Leu Pro Trp Thr Phe Gly Gln Gly Thr Lys
            595                 600                 605

Val Glu Ile Lys Arg
            610

<210> SEQ ID NO 2
<211> LENGTH: 234
<212> TYPE: PRT
<213> ORGANISM: Homo sapiens

<400> SEQUENCE: 2

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Thr Leu Ser
                20                  25                  30

Val Thr Pro Gly Asp Ser Val Ser Leu Ser Cys Arg Ala Ser Gln Ser
            35                  40                  45

Ile Ser Asn Asn Leu His Trp Tyr Gln Gln Lys Ser His Glu Ser Pro
        50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Val Tyr Phe Cys Gln Gln Ser Asn
            100                 105                 110

Thr Trp Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190
```

Tyr Ser Leu Ser Ser Thr Leu Thr Leu Ser Lys Ala Asp Tyr Glu Lys
    195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 3
<211> LENGTH: 1842
<212> TYPE: DNA
<213> ORGANISM: Homo sapiens

<400> SEQUENCE: 3

| | | | | |
|---|---|---|---|---|
| atggaatgga gctgggtctt tctcttcttc ctgtcagtaa cgactggtgt ccactcccag | | | | 60 |
| gtgcagctgc agcagcctgg tgccgagctc gtgaaacctg gcgcctccct gaagctgtcc | | | | 120 |
| tgcaagtcct ccggctacac cttcaccagc tactggatgc actgggtgcg acagaggcct | | | | 180 |
| ggccacggac tggaatggat cggcgagatc gaccccctccg actcctacaa ggactacaac | | | | 240 |
| cagaagttca aggacaaggc caccctgacc gtggacagat cctccaacac cgcctacatg | | | | 300 |
| cacctgtcct ccctgacctc cgacgactcc gccgtgtact actgcgccag agccatcaca | | | | 360 |
| accacccccct tcgatttctg gggccagggc accacactga cagtgtcctc cgcttccacc | | | | 420 |
| aagggccccct ccgtgtttcc tctggccct tccagcaagt ccacctctgg cggaacagcc | | | | 480 |
| gctctgggct gcctcgtgaa ggactacttc cccgagcctg tgaccgtgtc ctggaactct | | | | 540 |
| ggcgctctga catccggcgt gcacaccttc cctgctgtgc tgcagtctag cggcctgtac | | | | 600 |
| tccctgtcca gcgtcgtgac cgtgccttcc agctctctgg gcacccagac ctacatctgc | | | | 660 |
| aacgtgaacc acaagccttc caacaccaag gtggacaaga aggtggaacc caagtcctgc | | | | 720 |
| gacaagaccc acaccagccc tccaagccct gctcctcctg tggctggccc tagcgtgttc | | | | 780 |
| ctgttccctc caaagcccaa ggatacctg atgatctccc ggaccccga agtgacctgc | | | | 840 |
| gtggtcgtgg agtgtctca cgaggaccct gaagtgaagt tcaattggta cgtggacggc | | | | 900 |
| gtggaagtgc acaacgccaa gaccaagcct agagaggaac agtaccagtc cacctaccgg | | | | 960 |
| gtggtgtccg tgctgaccgt gctgcaccag gattggctga acggcaaaga gtacaagtgc | | | | 1020 |
| aaggtgtcca acaagcagct gcccagcccc atcgaaaaga ccatctccaa ggctaagggc | | | | 1080 |
| ggaggcggag ctggtggtgg cggagaagtg cagctggtgg aatctggcgg cggactggtg | | | | 1140 |
| cagcctggcg gatctctgag actgtcttgt gccgccagcg gctactcttt caccggctat | | | | 1200 |
| accatgaatt gggtgcgcca ggcccctgga aagggcctgg aatgggtggc cctgatcaac | | | | 1260 |
| ccctacaagg gcgtgaccac ctacgccgac tccgtgaagg gccggttcac catctccgtg | | | | 1320 |
| gacaagtcca gaataccgc ttacctgcag atgaactccc tgcgggccga ggacaccgct | | | | 1380 |
| gtgtattact gtgctagatc cggctactac ggcgacagcg attggtactt cgacgtgtgg | | | | 1440 |
| ggacagggaa ccctcgtgac tgtgtcatca ggcggcggtg gttctggcgg aggggatct | | | | 1500 |
| gggggcggtg gatccgatat ccagatgacc cagtccccca gctccctgtc tgcctctgtg | | | | 1560 |
| ggcgacagag tgaccatcac ctgtcgggcc tctcaggaca tccggaacta cctgaactgg | | | | 1620 |
| tatcagcaga agcccggcaa ggccccaag ctgctgatct actacacctc ccggctggaa | | | | 1680 |
| agcggcgtgc cctccagatt ctccggctct ggctctggaa ccgactatac cctgaccatc | | | | 1740 |
| tctagcctgc agcccgagga cttcgccacc tactactgcc agcagggcaa caccctgccc | | | | 1800 |
| tggaccttg gccagggaac aaaggtggaa atcaagcggt ga | | | | 1842 |

<210> SEQ ID NO 4
<211> LENGTH: 705
<212> TYPE: DNA
<213> ORGANISM: Homo sapiens

<400> SEQUENCE: 4

```
atggagaccg acaccctgct gctctgggtg ctgctgctct gggtgcccgg ctccaccgga      60
gacatcgtgc tgacccagtc tcccgccacc ctgtctgtga cccctggcga ctctgtgtcc     120
ctgtcctgca gagcctccca gtccatctcc aacaacctgc actggtatca gcagaagtcc     180
cacgagagcc ctcggctgct gattaagtac gccagccagt ctatctccgg catcccctcc     240
agattctccg gctctggctc tggcaccgac ttcaccctgt ccatcaactc cgtggaaacc     300
gaggacttcg cgtgtacttc tgccagcag tccaacacct ggccctacac ctttggcgga     360
ggcaccaagc tggaaatcaa gcggaccgtg gccgccccca gcgtgttcat cttccctccc     420
agcgacgagc agctgaagtc tggcaccgcc agcgtggtgt gcctgctgaa caacttctac     480
ccccgcgagg ccaaggtgca gtggaaggtg gacaacgccc tgcagagcgg caacagccag     540
gagagcgtga ccgagcagga ctccaaggac agcacctaca gcctgagcag caccctgacc     600
ctgagcaagg ccgactacga gaagcacaag gtgtacgcct gcgaggtgac ccaccaggga     660
ctgtctagcc ccgtgaccaa gagcttcaac cggggcgagt gctaa                     705
```

<210> SEQ ID NO 5
<211> LENGTH: 107
<212> TYPE: PRT
<213> ORGANISM: Mus musculus

<400> SEQUENCE: 5

```
Asp Ile Gln Met Thr Gln Ser Pro Ser Ser Leu Ser Ala Ser Leu Gly
1               5                   10                  15
Glu Arg Val Ser Leu Thr Cys Arg Ala Ser Gln Glu Ile Ser Gly Tyr
            20                  25                  30
Leu Ser Trp Leu Gln Gln Lys Pro Asp Gly Thr Ile Lys Arg Leu Ile
        35                  40                  45
Tyr Ala Ala Ser Thr Leu His Ser Gly Val Pro Lys Arg Phe Ser Gly
    50                  55                  60
Ser Arg Ser Gly Ser Asp Tyr Ser Leu Thr Ile Ser Arg Leu Glu Ser
65                  70                  75                  80
Glu Asp Val Ala Asp Tyr Tyr Cys Leu Gln Tyr Ala Ser Tyr Pro Phe
                85                  90                  95
Thr Phe Gly Ser Gly Thr Lys Leu Glu Ile Arg
            100                 105
```

<210> SEQ ID NO 6
<211> LENGTH: 321
<212> TYPE: DNA
<213> ORGANISM: Mus musculus

<400> SEQUENCE: 6

```
gacatccaga tgacccagtc tccatcctcc ttatctgcct ctctgggaga aagagtcagt      60
ctcacttgtc gggcaagtca ggaaattagt ggttacttaa gctggcttca gcagaaacca     120
gatggaacta ttaaacgcct gatctacgcc gcatccactt acattctggg tgtcccaaaa     180
aggttcagtg gcagtaggtc tgggtcagat tactctctca ccatcagcag gcttgagtct     240
gaagatgttg cagactatta ctgtctacaa tatgctagtt atccattcac gttcggctcg     300
```

```
gggacaaagt tggaaataag a                                              321
```

<210> SEQ ID NO 7
<211> LENGTH: 123
<212> TYPE: PRT
<213> ORGANISM: Mus musculus

<400> SEQUENCE: 7

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Thr Met Gly Val Gly Trp Ile Arg Gln Pro Ser Gly Lys Gly Leu Glu
        35                  40                  45

Trp Leu Leu His Ile Leu Trp Asn Asp Ser Lys Tyr Tyr Asn Pro Ala
    50                  55                  60

Leu Lys Ser Arg Leu Thr Ile Ser Lys Asp Thr Tyr Asn Lys Gln Val
65                  70                  75                  80

Phe Leu Lys Ile Ala Asn Val Asp Thr Ala Asp Thr Ala Thr Tyr Tyr
                85                  90                  95

Cys Ala Arg Ile Val Tyr Tyr Ser Thr Tyr Val Gly Tyr Phe Asp Val
            100                 105                 110

Trp Gly Ala Gly Thr Thr Val Thr Val Ser Ser
        115                 120
```

<210> SEQ ID NO 8
<211> LENGTH: 369
<212> TYPE: DNA
<213> ORGANISM: Mus musculus

<400> SEQUENCE: 8

```
caggttactc tgaaagagtc tggccctggg atattgcagc cctcccagac cctcagtctg    60
acttgttctt tctctgggtt ttctctgagc acttctacta tgggtgtagg ctggattcgt   120
cagccttcag ggaagggtct ggagtggctg ttacacattt tgtggaatga tagtaagtat   180
tataacccag ccctgaagag ccggctcaca atctccaagg atacctacaa caagcaggta   240
ttcctcaaga tcgccaatgt ggacactgca gatactgcca catactactg tgctcgaata   300
gtttactact ctacctacgt cgggtacttc gatgtctggg gcgcagggac cacggtcacc   360
gtctcctca                                                           369
```

<210> SEQ ID NO 9
<211> LENGTH: 111
<212> TYPE: PRT
<213> ORGANISM: Mus musculus

<400> SEQUENCE: 9

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Ser Pro
        35                  40                  45

Lys Leu Leu Ile Tyr Ala Val Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80
```

```
Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110
```

<210> SEQ ID NO 10
<211> LENGTH: 333
<212> TYPE: DNA
<213> ORGANISM: Mus musculus

<400> SEQUENCE: 10

```
gacattgtgc tgacccaatc tccagcttct ttggctgtgt ctctagggca gagggccacc    60
atctcctgca gagccagcga aagtgttgat aattatggca ttagttttat gaactggttc   120
caacagaaac caggacagtc acccaaactc ctcatctatg ctgtatccaa ccaaggatcc   180
ggggtccctg ccaggtttag tggcagtggg tctgggacag acttcagcct caacatccat   240
cctatggagg aggatgatac tgcaatgtat ttctgtcagc aaagtaagga ggttccgtgg   300
acgttcggtg gaggcaccaa gctggaaatc aaa                                333
```

<210> SEQ ID NO 11
<211> LENGTH: 116
<212> TYPE: PRT
<213> ORGANISM: Mus musculus

<400> SEQUENCE: 11

```
Glu Val Gln Leu Gln Gln Ser Gly Ala Glu Leu Val Arg Pro Gly Ala
1               5                   10                  15

Leu Val Lys Leu Ser Cys Lys Gly Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Arg Ile Asp Pro Glu Asn Asp Ile Thr Met Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Asn Gly Asn Phe Phe Ala Tyr Trp Gly Gln Gly Thr Leu Val
            100                 105                 110

Thr Val Ser Ala
        115
```

<210> SEQ ID NO 12
<211> LENGTH: 348
<212> TYPE: DNA
<213> ORGANISM: Mus musculus

<400> SEQUENCE: 12

```
gaggttcagc tgcagcagtc tggggctgag cttgtgaggc caggggcctt agtcaagttg    60
tcctgcaaag gttctggctt caacattaaa gactactata cactgggt gaagcagagg    120
cctgaacagg gcctggagtg gattggaagg attgatcctg agaatgatat tactatgtat   180
gacccgaagt tccagggcaa ggccagtata acagcagaca catcctccaa cacagcctac   240
ctgcagctca gcagcctgac atctgaggac actgccgtct attactgtgc tagaaatggt   300
aatttctttg cttactgggg ccaagggact ctggtcactg tctctgca               348
```

<210> SEQ ID NO 13
<211> LENGTH: 107
<212> TYPE: PRT
<213> ORGANISM: Mus musculus

<400> SEQUENCE: 13

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asn Ser Gly Val Pro Arg Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 14
<211> LENGTH: 321
<212> TYPE: DNA
<213> ORGANISM: Mus musculus

<400> SEQUENCE: 14
gacatccaga tgacccagtc tccatcctcc ttatctgcct ctctgggaga aagagtcagt      60
ctcacttgtc gggcaagtca ggaaattagt ggttacttaa gctggcttca gcagaaacca     120
gatggaacta ttaaacgcct gatctacgcc gcatccactt aaaattctgg tgtcccaaga     180
aggttcagtg gcagtaggtc tgggtcagat tattctctca ccatcagcag ccttgagtct     240
gaagattttg cagactatta ctgtctacaa tatgctagtt atccattcac gttcggctcg     300
gggacaaagt tggaaataaa a                                               321

<210> SEQ ID NO 15
<211> LENGTH: 124
<212> TYPE: PRT
<213> ORGANISM: Mus musculus

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

His Met Gly Val Gly Trp Ile Arg Gln Pro Ser Gly Lys Gly Leu Glu
        35                  40                  45

Trp Leu Leu His Ile Leu Trp Asn Asp Ser Val Tyr Tyr Asn Pro Ala
    50                  55                  60

Leu Lys Ser Arg Leu Thr Ile Ser Lys Asp Thr Tyr Asn Lys Gln Val
65                  70                  75                  80

Phe Leu Lys Ile Ala Asn Val Asp Thr Ala Asp Thr Ala Thr Tyr Tyr
                85                  90                  95

Cys Ala Arg Ile Val Tyr Tyr Gly Ile Ser Tyr Val Gly Tyr Phe Asp
            100                 105                 110

Val Trp Gly Ala Gly Thr Thr Val Thr Val Ser Ser

<210> SEQ ID NO 16
<211> LENGTH: 372
<212> TYPE: DNA
<213> ORGANISM: Mus musculus

<400> SEQUENCE: 16

```
caggttactc tgaaagagtc tggccctggg atattgcagc cctcccagac cctcagtctg    60
acttgttctt tctctgggtt ttcactgagc acttctcaca tgggtgtagg ctggattcgt   120
cagccttcag ggaagggtct ggagtggctg ttacacattt tgtggaatga tagtgtgtac   180
tataacccag ccctgaagag ccggctcaca atctccaagg atacctacaa caagcaggta   240
ttcctcaaga tcgccaatgt ggacactgca gatactgcca catactactg tgctcgaata   300
gtttactacg gtattagtta cgtcgggtac ttcgatgtct ggggcgcagg gaccacggtc   360
accgtctcct ca                                                       372
```

<210> SEQ ID NO 17
<211> LENGTH: 107
<212> TYPE: PRT
<213> ORGANISM: Mus musculus

<400> SEQUENCE: 17

```
Asp Thr Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Tyr Gly Phe Gln Ser Ile Ser Gly Ile Pro Ser Arg Phe Ser Gly
        50                  55                  60

Ser Gly Ser Gly Thr Asp Phe Thr Leu Arg Ile Asn Ser Val Glu Thr
 65                  70                  75                  80

Glu Asp Phe Gly Met Tyr Phe Cys Gln Gln Thr Asn Ser Trp Pro Leu
                85                  90                  95

Thr Phe Gly Ala Gly Thr Lys Leu Glu Leu Lys
               100                 105
```

<210> SEQ ID NO 18
<211> LENGTH: 321
<212> TYPE: DNA
<213> ORGANISM: Mus musculus

<400> SEQUENCE: 18

```
gatactgtgc taactcaatc tccagccacc ctgtctgtga ctccaggaga tagcgtcagt    60
ctttcctgca gggccagcca agtattagc aacaacctac actggtatca acaaaaatca   120
catgagtctc caaggcttct catcaagtat ggtttccagt ccatctctgg gatcccctcc   180
aggttcagtg gcagtggatc aggacagat ttcactctca gaatcaacag tgtggagact   240
gaagattttg gaatgtattt ctgtcaacag actaacagct ggccgctcac gttcggtgct   300
gggaccaagc tggagctgaa a                                             321
```

<210> SEQ ID NO 19
<211> LENGTH: 115
<212> TYPE: PRT
<213> ORGANISM: Mus musculus

<400> SEQUENCE: 19

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Ile Asp Tyr
            20                  25                  30

Asn Met Tyr Trp Val Lys Gln Ser His Gly Lys Ser Leu Glu Trp Ile
        35                  40                  45

Gly Tyr Ile Asn Pro Tyr Asn Gly Gly Thr Ser Asn Asn Gln Lys Phe
    50                  55                  60

Lys Asp Lys Ala Thr Leu Thr Val Asp Lys Ser Ser Ser Thr Ala Phe
65                  70                  75                  80

Met His Leu Asn Ser Leu Thr Ser Glu Asp Ser Ala Val Tyr Tyr Cys
                85                  90                  95

Ala Arg Gly Thr Thr Gly Asp Tyr Trp Gly Gln Gly Thr Thr Leu Thr
            100                 105                 110

Val Ser Ser
        115

<210> SEQ ID NO 20
<211> LENGTH: 345
<212> TYPE: DNA
<213> ORGANISM: Mus musculus

<400> SEQUENCE: 20
gagatccagc tgcagcagtc tggacctgaa ctggtgaagc ctggggcttc agtgaaggta      60
tcctgcaagg cttctggtta ctcattcatt gactacaaca tgtactgggt gaagcagagc     120
catggaaaga gccttgagtg gattggatat attaatcctt acaatggtgg tactagcaac     180
aaccagaagt tcaaggacaa ggccacattg actgttgaca gtcctccag cacagccttc      240 atgcatctca acagcctgac atctgaggac tctgcagtct attactgtgc aagaggtact     300
acgggtgact actggggcca aggcaccact ctcacagtct cctca                     345

<210> SEQ ID NO 21
<211> LENGTH: 111
<212> TYPE: PRT
<213> ORGANISM: Mus musculus

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 22
<211> LENGTH: 333
<212> TYPE: DNA

<213> ORGANISM: Mus musculus

<400> SEQUENCE: 22

```
gacattgtgc tgacccaatc tccagcttct ttggctgtgt ctctagggca gagggccacc    60
atctcctgca gagccagcga aagtgttgat aattatggca ttagtttat gaactggttc    120
caacagaaac caggacagcc acccaaactc ctcatctatg ctgcatccaa ccaaggatcc    180
ggggtccctg ccaggtttag tggcagtggg tctgggacag acttcagcct caacatccat    240
cctatggagg aggatgatac tgcaatgtat ttctgtcagc aaagtaagga ggttccgtgg    300
acgttcggtg gaggcaccaa gctggaaatc aaa                                 333
```

<210> SEQ ID NO 23
<211> LENGTH: 119
<212> TYPE: PRT
<213> ORGANISM: Mus musculus

<400> SEQUENCE: 23

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Ala Tyr Tyr Ser Lys Arg Asp Asp Tyr Trp Gly Gln Gly
            100                 105                 110

Thr Thr Leu Thr Val Ser Ser
        115

<210> SEQ ID NO 24
<211> LENGTH: 357
<212> TYPE: DNA
<213> ORGANISM: Mus musculus

<400> SEQUENCE: 24

```
caggtccaac tgcagcagcc tggggctgag cttgtgatgc ctggggcttc agtgaagctg    60
tcctgcaagg cttctggcta caccttcacc agctactgga tgcactgggt gaagcagagg    120
cctggacaag ccttgagtg gatcggagag attgatcctt ctgatagtta tactaactac    180
aatcaaaagt tcaagggcaa ggccacattg actgtagaca atcctccag cacagcctac    240
atgcagctca gcagcctgac atctgaggac tctgcggtct attactgtgc aagatcagcc    300
tactatagta aagggatga ctactggggc caaggcacca ctctcacagt ctcctca       357
```

<210> SEQ ID NO 25
<211> LENGTH: 107
<212> TYPE: PRT
<213> ORGANISM: Mus musculus

<400> SEQUENCE: 25

Asp Ile Gln Met Thr Gln Ser Pro Ser Ser Leu Ser Ala Ser Leu Gly
1               5                   10                  15

```
Glu Arg Val Ser Leu Thr Cys Arg Ala Ser Gln Glu Ile Ser Gly Tyr
                20                  25                  30

Leu Ser Trp Leu Gln Gln Lys Pro Asp Gly Thr Ile Lys Arg Leu Ile
            35                  40                  45

Tyr Ala Ala Ser Thr Leu His Ser Gly Val Pro Lys Arg Phe Ser Gly
 50                  55                  60

Ser Arg Ser Gly Ser Asp Tyr Ser Leu Thr Ile Ser Arg Leu Glu Ser
 65                  70                  75                  80

Glu Asp Val Ala Asp Tyr Tyr Cys Leu Gln Tyr Ala Ser Tyr Pro Phe
                 85                  90                  95

Thr Phe Gly Ser Gly Thr Lys Leu Glu Ile Arg
                100                 105
```

<210> SEQ ID NO 26
<211> LENGTH: 321
<212> TYPE: DNA
<213> ORGANISM: Mus musculus

<400> SEQUENCE: 26

```
gacatccaga tgacccagtc tccatcctcc ttatctgcct ctctgggaga aagagtcagt    60
ctcacttgtc gggcaagtca ggaaattagt ggttacttaa gctggcttca gcagaaacca   120
gatggaacta ttaaacgcct gatctacgcc gcatccactt acattctggg tgtcccaaaa   180
aggttcagtg gcagtaggtc tgggtcagat tactctctca ccatcagcag gcttgagtct   240
gaagatgttg cagactatta ctgtctacaa tatgctagtt atccattcac gttcggctcg   300
gggacaaagt tggaaataag a                                             321
```

<210> SEQ ID NO 27
<211> LENGTH: 123
<212> TYPE: PRT
<213> ORGANISM: Mus musculus

<400> SEQUENCE: 27

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
                20                  25                  30

Thr Met Gly Val Gly Trp Ile Arg Gln Pro Ser Gly Lys Gly Leu Glu
            35                  40                  45

Trp Leu Leu His Ile Leu Trp Asn Asp Ser Lys Tyr Tyr Asn Pro Ala
 50                  55                  60

Leu Lys Ser Arg Leu Thr Ile Ser Lys Asp Thr Tyr Asn Lys Gln Val
 65                  70                  75                  80

Phe Leu Lys Ile Ala Asn Val Asp Thr Ala Asp Thr Ala Thr Tyr Tyr
                 85                  90                  95

Cys Ala Arg Ile Val Tyr Tyr Ser Thr Tyr Val Gly Tyr Phe Asp Val
                100                 105                 110

Trp Gly Ala Gly Thr Thr Val Thr Val Ser Ser
            115                 120
```

<210> SEQ ID NO 28
<211> LENGTH: 369
<212> TYPE: DNA
<213> ORGANISM: Mus musculus

<400> SEQUENCE: 28

```
caggttactc tgaaagagtc tggccctggg atattgcagc cctcccagac cctcagtctg    60
```

-continued

```
acttgttctt tctctgggtt ttctctgagc acttctacta tgggtgtagg ctggattcgt        120
cagccttcag ggaagggtct ggagtggctg ttacacattt tgtggaatga tagtaagtat        180
tataacccag ccctgaagag ccggctcaca atctccaagg ataacctacaa caagcaggta       240 ttcctcaaga tcgccaatgt ggacactgca gatactgcca catactactg tgctcgaata        300
gtttactact ctacctacgt cgggtacttc gatgtctggg gcgcagggac cacggtcacc        360
gtctcctca                                                                369
```

MONOCLONAL ANTIBODIES TO HUMAN FLT3/FLK2 RECEPTOR PROTEIN

CROSS-REFERENCE TO RELATED APPLICATIONS

This application is a continuation-in-part of U.S. patent application Ser. No. 16/091,139, filed Oct. 4, 2018, which is a 35 U.S.C. § 371 national stage filing of International Application No. PCT/US2017/025951, filed Apr. 4, 2017, which claims the benefit of priority to U.S. Provisional Application No. 62/317,906, filed Apr. 4, 2016, entitled "Method of Eliminating Hematopoietic Stem Cells/Hematopoietic Progenitors (HSC/HP) in a Patient Using Bi-Specific Antibodies." The entire contents of each of the aforementioned applications are incorporated by reference herein in their entireties.

SEQUENCE LISTING

The instant application contains a Sequence Listing which has been submitted electronically in ASCII format and is hereby incorporated by reference in its entirety. Said ASCII copy, created on Jun. 17, 2019, is named 128557_00103_Sequence_Listing.txt and is 30,480 bytes in size.

FIELD OF THE INVENTION

The described invention generally relates to hematopoietic cell transplantation, therapeutic antibody preparations and their uses.

BACKGROUND OF THE INVENTION

Hematopoietic Stem Cells

The hematopoietic stem cell is the common ancestor of all blood cells. As multipotent cells, they can differentiate into multiple cell lineages, but not all the lineages derived from the three germ layers. Hematopoietic stem cell differentiation gives rise to the lymphoid and myeloid cell lineages, the two major branches of hematopoiesis. (Kondo, M. "Lymphoid and myeloid lineage commitment in multipotent hematopoietic progenitors," Immunol. Rev. 2010 November; 238(1): 37-46). Lymphoid lineage cells include T, B, and natural killer (NK) cells. The myeloid lineage includes megakaryocytes and erythrocytes (MegE) as well as different subsets of granulocytes (neutrophils, eosinophils and basophils), monocytes, macrophages, and mast cells (GM), which belong to the myeloid lineage (Id. citing Kondo M, et al. Biology of hematopoietic stem cells and progenitors: implications for clinical application. Ann. Rev Immunol. 2003; 21:759-806., Weissman I L. Translating stem and progenitor cell biology to the clinic: barriers and opportunities. Science (New York, N.Y. 2000 Feb. 25; 287(5457): 1442-6; see also Iwaskaki, H. and Akashi, K. "Myeloid lineage commitment from the hematopoietic stem cell," Immunity 26(6) June 2007, 726-40).

HSCs present self-renewal potential and differentiation capacity into blood lineages; i.e., when stem cells divide, 50% of the daughter cells, on average, are committed with a cell lineage, while the remaining 50% do not differentiate. The process maintains the same number of stem cells by asymmetric cell division, so that each dividing stem cell originates one new stem cell and one differentiated cell. In contrast, in symmetric division, the stem cells originate 100% of identical stem cells. (Gordon, M. *Stem cells and haemopoiesis*. In: Hoffbrand, V., Catovsky, D., Tuddenham, E. G., 5th ed. Blackwell Publishing, (2005): Differential niche and Wnt requirements during acute myeloid leukemia, pp. 1-12. New York.).

The lymphoid and myeloid lineages are separable at the progenitor level. Common lymphoid progenitors (CLPs) can differentiate into all types of lymphocytes without noticeable myeloid potential under physiological conditions (Kondo M, Scherer D C, Miyamoto T, King A G, Akashi K, Sugamura K, et al. Cell-fate conversion of lymphoid-committed progenitors by instructive actions of cytokines. Nature. 2000 Sep. 21; 407(6802):383-6), although some myeloid related genes might be detected in CLPs, depending on the experimental conditions (Delogu A, Schebesta A, Sun Q, Aschenbrenner K, Perlot T, Busslinger M. Gene repression by Pax5 in B cells is essential for blood cell homeostasis and is reversed in plasma cells. Immunity. 2006 March; 24(3):269-81).

Similarly, common myeloid progenitors (CMPs) can give rise to all classes of myeloid cells with no or extensively low levels of B-cell potential (Akashi K, Traver D, Miyamoto T, Weissman I L. A clonogenic common myeloid progenitor that gives rise to all myeloid lineages. Nature. 2000 Mar. 9; 404(6774):193-7). Another cell type, dendritic cells (DCs), is not clearly grouped either in lymphoid or myeloid lineage, because DC can arise from either CLPs or CMPs (Manz M G, Traver D, Miyamoto T, Weissman I L, Akashi K. Dendritic cell potentials of early lymphoid and myeloid progenitors. Blood. 2001 Jun. 1; 97(11):3333-41, Traver D, Akashi K, Manz M, Merad M, Miyamoto T, Engleman E G, et al. Development of CD8alpha-positive dendritic cells from a common myeloid progenitor. Science (New York, N.Y. 2000 Dec. 15; 290(5499):2152-4). CMPs can proliferate and differentiate into megakaryocyte-erythrocyte (MegE) progenitors and granulocyte-monocyte (GM) progenitors, which further give rise to megakaryocytes, erythrocytes, granulocytes, monocytes and others. (Iwasaki H, Akashi K. Myeloid lineage commitment from the hematopoietic stem cell. Immunity. 2007; 26:726-740).

It is likely that differences in the expression levels of transcription factors determine the lineage affiliation of a differentiating cell. The transcription factors PU.1 and GATA-1 have been implicated in myeloid and erythroid/megakaryocyte lineage differentiation, respectively (Gordon, M. Stem cells and haemopoiesis. In: Hoffbrand, V., Catovsky, D., Tuddenham, E. G., 5th ed. Blackwell Publishing, (2005): Differential niche and Wnt requirements during acute myeloid leukemia, pp. 1-12. New York.).

Characterization of HSCs

HSCs are undifferentiated and resemble small lymphocytes. A large fraction of HSCs is quiescent, in the G0 phase of the cell cycle, which protects them from the action of cell cycle-dependent drugs. The quiescent state of stem cells is maintained by transforming growth factor-β (TGF-β). The activity of TGF-β is mediated by p53, a tumor suppressor gene that regulates cell proliferation and targets the cyclin-dependent kinase inhibitor p21 (Gordon, M. *Stem cells and haemopoiesis*. In: Hoffbrand, V., Catovsky, D., Tuddenham, E. G., 5th ed. Blackwell Publishing, (2005): Differential niche and Wnt requirements during acute myeloid leukemia, pp. 1-12. New York.). Quiescence of HSCs is critical not only for protecting the stem cell compartment and sustaining stem cell pools during long periods of time, but also for minimizing the accumulation of replication-associated mutations. Many of the intrinsic transcriptional factors that maintain HSCs quiescence are found to be associated with leukemias. For example, chromosomal translocations resulting in the fusion of FoxOs and myeloid/lymphoid or mixed lineage leukemia have been reported in acute myeloid leukemias (See, e.g., Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1).

The majority of normal HSCs are present among the CD34+/CD38−/CD90+ bone marrow cell fractions with some HSCs also observed among CD34−/Lin− cells. CD34+/CD38+ cell fractions contain some HSCs endowed with short-term repopulating activity. Other recognized markers include the tyrosine kinase receptor c-kit (CD117) coupled with a lack of terminal differentiation markers such as CD4 and CD8 (Rossi et al., Methods in Molecular Biology (2011) 750(2): 47-59).

Classification of HSCs.

The hematopoietic stem cell pool can be subdivided into three main groups: (1) short-term HSCs, capable of generating clones of differentiating cells for only 4-6 weeks; (2) intermediate-term HSCs, capable of sustaining a differentiating cell progeny for 6-8 months before becoming extinct; and (3) long-term HSCs, capable of maintaining hematopoiesis indefinitely. (Testa U. Annals of Hematology (2011) 90(3): 245-271).

Hematopoiesis

Hematopoiesis is a highly coordinated process wherein HSCs differentiate into mature blood cells supported by a specialized regulatory microenvironment, consisting of components which control the fate specification of stem and progenitor cells, as well as maintaining their development by supplying the requisite factors ("niche"). The term "bone marrow (BM) niche" as used herein refers to a well-organized architecture composed of elements (e.g., osteoblasts, osteoclasts, bone marrow endothelial cells, stromal cells, adipocytes and extracellular matrix proteins (ECM)) that play an essential role in the survival, growth and differentiation of diverse lineages of blood cells. The bone marrow niche is an important post-natal microenvironment in which HSCs proliferate, mature and give rise to myeloid and lymphoid progenitors.

Bone marrow (BM) is present in the medullary cavities of all animal bones. It consists of a variety of precursor and mature cell types, including hematopoietic cells (the precursors of mature blood cells) and stromal cells (the precursors of a broad spectrum of connective tissue cells), both of which appear to be capable of differentiating into other cell types. The mononuclear fraction of bone marrow contains stromal cells, hematopoietic precursors, and endothelial precursors.

Unlike secondary lymphoid organs such as spleen with distinct gross structures including red and white pulp, BM has no clear structural features, except for the endosteum that contains osteoblasts. The endosteum region comes in contact with calcified hard bones and provides a special microenvironment which is necessary for the maintenance of HSC activity (Kondo M, Immunology Reviews (2010) 238(1): 37-46; Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1).

Within the niche, HSCs are believed to receive support and growth signals originating from several sources, including: fibroblasts, endothelial and reticular cells, adipocytes, osteoblasts and mesenchymal stem cells (MSCs). The main function of the niche is to integrate local changes in nutrients, oxygen, paracrine and autocrine signals and to change HSCs quiescence, trafficking, and/or expansion in response to signals from the systemic circulation (Broner, F. & Carson, M C. Topics in bone biology. Springer. 2009; 4: pp. 2-4. New York, USA.).

Although the nature of true MSCs remains misunderstood, CXC chemokine ligand 12 (CXCL12)-expressing CD146 MSCs were recently reported to be self-renewing progenitors that reside on the sinusoidal surfaces and contribute to organization of the sinusoidal wall structure, produce angiopoietin-1 (Ang-1), and are capable of generating osteoblasts that form the endosteal niche (Konopleva, M Y, & Jordan, C T, Biology and Therapeutic Targeting (2011) 9(5): 591-599). These CXCL12 reticular cells may serve as a transit pathway for shuttling HSCs between the osteoblastic and vascular niches where essential but different maintenance signals are provided.

Cytokines and chemokines produced by bone marrow MSCs concentrate in particular niches secondary to varying local production and through the effects of cytokine-binding glycosaminoglycans. Of these, CXCL12/stromal cell-derived factor-1 alpha positively regulates HSCs homing, while transforming growth factors FMS-like tyrosine kinase 3 (Flt3) ligand and Ang-1 act as quiescence factors (See, e.g., Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1). CXCL12-CXCR4 signaling is involved in homing of HSCs into BM during ontogeny as well as survival and proliferation of colony-forming progenitor cells. The CXCR4-selective antagonist-induced mobilization of HSCs into the peripheral blood further indicates a role for CXCL12 in retaining HSCs in hematopoietic organs.

BM engraftment involves subsequent cell-to-cell interactions through the BMSC-produced complex extracellular matrix. Thus, vascular cell adhesion molecule-1 (VCAM-1) or fibronectin is critical for adhesion to the BM derived MSCs. In this way, the control of hematopoietic stem cell proliferation kinetics is critically important for the regulation of correct hematopoietic cell production. These control mechanisms could be classified as intrinsic or extrinsic to the stem cells, or a combination of both (See, e.g., Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1).

HSC self-renewal and differentiation can be controlled by external factors (extrinsic control), such as cell-cell interactions in the hematopoietic microenvironment or cytokines, such as SCF (stem cell factor) and its receptor c-kit, Flt-3 ligand, TGF-$\beta$, TNF-$\alpha$ and others. Cytokines regulate a variety of hematopoietic cell functions through the activation of multiple signal transduction pathways. The major pathways relevant to cell proliferation and differentiation are the Janus kinase (Jak)/signal transducers and activators of transcription (STATs), the mitogen-activated protein (MAP) kinase and the phosphatidylinositol (PI) 3-kinase pathways (Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1).

In addition, expression of other transcription factors, such as, stem cell leukemia (SCL) hematopoietic transcription factor; GATA-2; and gene products involved in cell cycle control, such as the cyclin dependent kinase inhibitors (CKIs) p16, p21 and p27 have been shown to be essential for hematopoietic cell development from the earliest stages (intrinsic control), (Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1).

Notch-1-Jagged pathway may serve to integrate extracellular signals with intracellular signaling and cell cycle control. Notch-1 is a surface receptor on hematopoietic stem cell membranes that binds to its ligand, Jagged, on stromal cells. This results in cleavage of the cytoplasmic portion of Notch-1, which can then act as a transcription factor (Gordon, M. *Stem cells and haemopoiesis*. In: Hoffbrand, V., Catovsky, D., Tuddenham, E. G., 5th ed. Blackwell Publishing, (2005): Differential niche and Wnt requirements during acute myeloid leukemia, pp. 1-12. New York.).

Disorders that are Treated Using Bone Marrow (BM)/Hematopoietic Stem Cell (HSC) Transplantation Disorders that are treated using Bone Marrow (BM)/Hematopoietic Stem Cell (HSC) transplantation include, without limitation, Acute Myeloid Leukemia (AML), Acute Lymphoblastic Leukemia (ALL), Chronic Lymphocytic Leukemia (CLL), Chronic Myeloid Leukemia (CML), peripheral T cell lymphoma, follicular lymphoma, diffuse large B cell lymphoma, Hodgkin lymphoma, non-Hodgkin lymphoma, neuroblastoma, non-malignant inherited and acquired marrow disorders (e.g. sickle cell anemia, beta-thalassemia major, refractory Diamond-Blackfan anemia, myelodysplastic syndrome, idiopathic severe aplastic anemia, paroxysmal nocturnal hemoglobinuria, pure red cell aplasia, Fanconi anemia, amegakaryocytosis, or congenital thrombocytopenia), multiple myeloma, and Severe Combined Immunodeficiency (SCID).

Hematopoietic Malignancies

Most hematopoietic malignancies comprise functionally heterogeneous cells, with only a subset, known as cancer stem cells, responsible for tumor maintenance. Cancer stem cells are so named because they possess qualities reminiscent of normal tissue stem cells including self-renewal, prolonged survival, and the ability to give rise to cells with more differentiated characteristics (Jones R J and Armstrong S A, Biol Blood Marrow Transplant. 2008 January; 14 (Supplement 1): 12-16).

A transforming event in hematopoietic stem cells can produce several different malignancies, including, without limitation, chronic myeloid leukemia, myelodysplastic syndrome, acute myeloid leukemia, and probably even acute lymphocytic leukemia, depending on the degree of differentiation associated with the oncogenic hit (Jones R J and Armstrong S A, Biol Blood Marrow Transplant. 2008 January; 14 (Supplement 1): 12-16).

The cancer stem cell concept is based on the idea that tumors of a specific tissue often appear to "attempt" to recapitulate the cellular heterogeneity found in the tissues of origin, and thus there are cells in the tumor that are stem-cell like giving rise to the varied cell types. A fundamental test for this hypothesis is whether tumor cells can be separated into those that have the ability to regenerate the tumor, and those that do not possess this ability. This cellular hierarchy has been most clearly demonstrated in acute myelogenous leukemias where some AMLs possess cells with a unique immunophenotype that are able to initiate leukemias in immunodeficient mice whereas most cells are unable to initiate leukemia development. Furthermore, the cells that initiate leukemias also give rise to cells that have lost tumor-initiating activity and thus recapitulate the cellular heterogeneity found in the original tumor (Lapidot T et al., Nature. 1994; 367: 645-648; Bonnet D et al., Nat Med. 1997; 3: 730-737).

Acute Myeloid Leukemia

Acute myeloid leukemia (AML) is a clonal disorder characterized by arrest of differentiation in the myeloid lineage coupled with an accumulation of immature progenitors in the bone marrow, resulting in hematopoietic failure (Pollyea D A et al., British Journal of Haematology (2011) 152(5): 523-542). There is wide patient-to-patient heterogeneity in the appearance of the leukemic blasts. The discovery of leukemia-initiating cells in acute myeloid leukemias (AMLs) started with the discovery that the large majority of AML blasts do not proliferate and only a small minority is capable of forming new colonies (Testa U, Annals of Hematology (2011) 90(3): 245-271). A common feature to all AML cases is the arrested aberrant differentiation leading to an accumulation of more than 20% blast cells in the bone marrow (Gilliland, D G and Tallman M S, Cancer Cell (2002) 1(5): 417-420).

More than 80% of myeloid leukemias are associated with at least one chromosomal rearrangement (Pandolfi P P, Oncogene (2001) 20(40): 5726-5735), and over 100 different chromosomal translocations have been cloned (Gilliland, D G and Tallman M S, Cancer Cell (2002) 1(5): 417-420). These translocations frequently involve genes encoding transcription factors that have been shown to play an important role in hematopoietic lineage development. Thus, alteration of the transcriptional machinery appears to be a common mechanism leading to arrested differentiation (Pandolfi P P, Oncogene (2001) 20(40): 5726-5735; Tenen D G, Nature Reviews of Cancer (2003) 3(2): 89-101).

Clinical investigation and experimental animal models suggest that at least two genetic alterations are required for the clinical manifestation of acute leukemia. According to the model proposed by Gilliland & Tallman (Cancer Cell (2002) 1(5): 417-420), cooperation between class I activating mutations and class II mutations that induce termination of differentiation give rise to AML. The class I mutations, such as mutations in the receptor tyrosine kinase genes FLT3 and KIT, RAS family members, and loss of function of neurofibromin 1, confer proliferative and/or survival advantage to hematopoietic progenitors, typically as a consequence of aberrant activation of signal transduction pathways. The class II mutations lead to a halt in differentiation via interference with transcription factors or co-activators (Frankfurt 0 et al., Current Opinion in Oncology (2007) 19(6): 635-649).

While the leukemia stem cell (LSC) appears to share many of the cell surface markers previously identified for HSC such as CD34, CD38, HLA-DR, and CD71, several groups have reported surface markers that are differentially expressed in the two populations.

For example, CD90 or Thy-1 has been described as potentially specific of the LSC compartment. Thy-1 is downregulated in normal hematopoiesis as the most primitive stem cells progress toward the progenitor stage. (Hope K J et al., Archives of Medical Research (2003) 34(6): 507-514).

The interaction between CXCL12 (stromal cell-derived factor-1 alpha) and its receptor CXCR4 on leukemic progenitor cells contributes to their homing to the bone marrow microenvironment. CXCR4 levels are significantly elevated in leukemic cells from patients with AML, and CXCR4 expression is associated with poor outcome (Konopleva M Y and Jordan C T, Biology and Therapeutic Targeting (2011) 29(5): 591-599).

Constitutive activation of the nuclear factor kappa β (NF-kβ) pathway in primary human AML stem cells provided evidence that NF-kβ plays a significant role in the overall survival of LSCs as well as AML cell types in general. (Konopleva M Y and Jordan C T, Biology and Therapeutic Targeting (2011) 29(5): 591-599).

FLT3, a member of the class III tyrosine kinase receptor family, is expressed in normal hematopoietic progenitors as well as in leukemic blasts, and it plays an important role in cell proliferation, differentiation, and survival. Activation of the FLT3 receptor by the FLT3 ligand leads to receptor dimerization and phosphorylation, and activation of downstream signaling pathways, including the Janus kinase (JAK) 2 signal transducer (JAK2), signal transducer and activator of transcription (STAT) 5, and mitogen-activated protein kinase (MAPK) pathways. Mutations in the FLT3 gene, found in approximately 40% of patients with AML, are believed to promote its autophosphorylation and constitutive activation, leading to ligand-independent proliferation (Frankfurt 0 et al., Current Opinion in Oncology (2007) 19(6): 635-649).

Lymphoid Malignancies

Self-renewal capacity in most tissues is lost as cells progress through their normal stages of differentiation; for example, myeloid lineage blood cells beyond the level of hematopoietic stem cells no longer possess self-renewal capacity. A notable exception to differentiation-associated loss of self-renewal is the lymphoid system, where self-renewal capacity is preserved until the memory lymphocyte stage in order to maintain life-long immune memory (Fearon D T et al., Science. 2001; 293: 248-250; Luckey C J et al., Proc Natl Acad Sci USA. 2006; 103: 3304-3309). Somatic hypermutation serves as a marker for the stage of differentiation at which B cell malignancies arise. In general, the presence of somatic hypermutation identifies a tumor as having arisen in germinal center or post-germinal center B cells, while the absence of mutation identifies pre-germinal center B cells. In contrast to myeloid malignancies but consonant with the lineage's preserved self-renewal capacity, immunoglobulin (Ig) mutation patterns suggest that B cell malignancies can arise from cells throughout the stages of B cell differentiation (Lapidot T et al., Nature. 1994; 367: 645-648; Bonnet D and Dick J E, Nat Med. 1997; 3: 730-737; Jones R J et al., J Natl Cancer Inst. 2004; 96: 583-585).

Multiple myeloma (MM) has generally been considered a disease of malignant plasma cells with many of the clinical consequences of the disease resulting from the plasma cell bulk. However, normal plasma cells are terminally differentiated and lack self-renewal capacity and it has been clear for over 30 years that only a minority of cells from mouse and human MM were clonogenic. These rare clonogenic cells have been termed "tumor stem cells" (Park C H et al., J Natl Cancer Inst. 1971; 46: 411-422; Hamburger A W and Salmon S E, Science. 1977; 197: 461-463). MM plasma cells arise from a small population of self-renewing cancer stem cells that resemble memory B cells. Not only do these clonotypic B cells circulate in most patients but they also are resistant to many standard anti-MM agents, and thus appear to be responsible for most disease relapses (Matsui W H et al., Blood. 2004; 103: 2332-2336; Kukreja A et al., J Exp Med. 2006; 203: 1859-1865; Jones R J and Armstrong S A, Biol Blood Marrow Transplant. 2008 January; 14 (Supplement 1): 12-16).

Reed-Sternberg (RS) cells, the hallmark of Hodgkin's lymphoma (HL), are the only blood cells other than plasma cells to occasionally express CD138 (Carbone A et al., Blood. 1998; 92: 2220-2228). It has been shown that HL cell lines include a small population of cells that lack the RS markers CD15 and CD30 present on the rest of the cells, while expressing markers consistent with a memory B cell phenotype (Newcom S R et al., Int J Cell Cloning. 1988; 6: 417-431; Jones R J et al., Blood. 2006; 108: 470). This small subpopulation of phenotypic memory B cells possessed all of the clonogenic capacity within the HL cell lines. Most HL patients, including those with early stage disease, harbor circulating memory B cells with the same clonal Ig gene rearrangement as the patients' RS cells (Jones R J et al., Blood. 2006; 108: 470; Jones R J and Armstrong S A, Biol Blood Marrow Transplant. 2008 January; 14 (Supplement 1): 12-16). These data suggest that these clonotypic memory B cells likely represent the HL stem cells.

Hematopoietic stem cells (HSCs) are used in bone marrow transplantation for treatment of hematological malignancies as well as nonmalignant disorders (Warner et al, Oncogene (2004) 23(43): 7164-7177). Until researchers discovered which cellular components were responsible for the engraftment of the donor hematopoietic and immune systems in marrow-ablated patients, bone marrow (BM) had been transplanted as an unfractionated cell pool for many years (See, e.g., Sérgio Paulo Bydlowski and Felipe de Lara Janz (2012). Hematopoietic Stem Cell in Acute Myeloid Leukemia Development, Advances in Hematopoietic Stem Cell Research, Dr. Rosana Pelayo (Ed.), ISBN: 978-953-307-930-1).

Preparation or conditioning of a patient for bone marrow/hematopoietic stem cell (BM/HSC) transplant is a critical element of the procedure. It serves two main purposes: (1) it provides adequate immunosuppression of the patient and clears sufficient niche space in the bone marrow for the transplanted HSC, which allows transplanted cells to engraft in the recipient; and (2) it often helps to eradicate the source of the malignancy.

Conditioning of patients has traditionally been achieved by administering maximally tolerated doses of a cocktail of chemotherapeutic agents with or without radiation. Components of the cocktail are often chosen to have non-overlapping toxicities. All preparative regimens currently in use are toxic and have severe side effects that can be life threatening. Among these side effects are mucositis, nausea and vomiting, alopecia, diarrhea, rash, peripheral neuropathies, infertility, pulmonary toxicities and hepatic toxicities. Many of these side effects are especially dangerous for older and sick patients, and often become a decisive component in deciding whether a patient will receive a transplant.

Thus, a need exists to prepare or condition patients eligible for bone marrow/hematopoietic stem cell (BM/HSC) transplant without these toxicities. The described invention provides compositions and methods for eliminating hematopoietic stem cells/hematopoietic progenitors (HSC/HP) in a patient using bi-specific antibodies that bind to human tyrosine kinase receptor FLT3/FLK2 receptor protein and to CD3 receptor protein expressed on T-cells.

SUMMARY OF THE INVENTION

According to one aspect, the described invention provides a method for preparing or conditioning a patient in need thereof for hematopoietic cell transplantation comprising: providing a recombinant single chain bi-specific antibody that binds to both human FLT3 and human CD3, and administering a therapeutic amount of a pharmaceutical composition comprising the bi-specific antibody to the patient; wherein the therapeutic amount is effective: to reduce by at least 90% a level in peripheral blood of a cell population expressing one or more of CD45, CD3, FLT3, CD19, CD33, and to reduce toxicity of protocols for preparing or conditioning the patient.

According to one embodiment, an amino acid sequence of a heavy chain of an antigen-binding portion of the bispecific antibody that binds FLT3 is SEQ ID NO: 1 and an amino acid sequence of a light chain of the antigen-binding portion of the bispecific antibody that binds FLT3 is SEQ ID NO: 2. According to another embodiment, the bi-specific antibody comprises a monoclonal antibody that reacts with a subunit of human CD3. According to another embodiment, the bi-specific antibody or antigen-binding portion thereof comprises an isotype selected from the group consisting of an immunoglobulin G (IgG), an IgM, an IgE, an IgA, and an IgD isotype.

According to one embodiment, the effective amount comprises 0.01 mg/kg to 10 mg/kg, better 0.05 mg/kg to 2 mg/kg, better 0.1 mg/kg to 0.5 mg/kg, better 0.1 mg/kg to 0.3 mg/kg, better 0.1 mg/kg.

According to one embodiment, the patient in need thereof is suffering from acute myeloid leukemia (AML), acute lymphoblastic leukemia (ALL), chronic myeloid leukemia (CLL), CML, peripheral T cell lymphoma, follicular lymphoma, diffuse large B cell lymphoma, Hodgkin lymphoma, non-Hodgkin lymphoma, neuroblastoma, a non-malignant inherited and acquired marrow disorder, multiple myeloma, or SCID. According to another embodiment, the non-malignant inherited and acquired marrow disorder is selected from sickle cell anemia, beta-thalassemia major, refractory Diamond-Blackfan anemia, myelodysplastic syndrome, idiopathic severe aplastic anemia, paroxysmal nocturnal hemoglobinuria, pure red cell aplasia, Fanconi anemia, amegakaryocytosis, and congenital thrombocytopenia.

According to one embodiment, the composition further comprises an antitumor agent.

According to one embodiment, the bispecific antibody is a humanized antibody.

According to another aspect, the described invention provides a method for preparing a recombinant single chain bi-specific antibody that binds to both human FLT3 and human CD3 comprising: joining a C-terminus of an Fab antigen-binding fragment of an Flt3 monoclonal antibody to a CH2 domain of IgG1, and joining to the CH2 domain of the IgG1 a single chain variable fragment (ScFv) of a monoclonal antibody that reacts with a subunit of human CD3 (UCHT1).

According to another aspect, the described invention provides a recombinant single chain bi-specific antibody that binds to both human FLT3 and human CD3 comprising: a C-terminus of an Fab antigen-binding fragment of an Flt3 monoclonal antibody that is joined to a CH2 domain of IgG1, and a single chain variable fragment (ScFv) of a monoclonal antibody that reacts with a subunit of human CD3 (UCHT1) joined to the CH2 domain of the IgG1.

According to one embodiment, an amino acid sequence of a heavy chain binding domain of the Fab antigen-binding fragment is SEQ ID NO: 1 (H3113) and an amino acid sequence of a light chain binding domain of the Fab antigen-binding fragment is SEQ ID NO: 2 (L3133).

According to another aspect, the described invention provides a monoclonal antibody or antigen binding fragment thereof, wherein an amino acid sequence of a light chain of an antigen-binding portion of the antibody or fragment thereof that binds to human FLT3/FLK2 receptor protein is SEQ ID NO: 5 and an amino acid sequence of a heavy chain of the antigen-binding portion of the antibody or fragment thereof that binds to human FLT3/FLK2 receptor protein is SEQ ID NO: 7.

According to another aspect, the described invention provides a monoclonal antibody or antigen binding fragment thereof, wherein an amino acid sequence of a light chain of an antigen-binding portion of the antibody or fragment thereof that binds to human FLT3/FLK2 receptor protein is SEQ ID NO: 9 and an amino acid sequence of a heavy chain of the antigen-binding portion of the antibody or fragment thereof that binds to human FLT3/FLK2 receptor protein is SEQ ID NO: 11.

According to another aspect, the described invention provides a monoclonal antibody or antigen binding fragment thereof, wherein an amino acid sequence of a light chain of an antigen-binding portion of the antibody or fragment thereof that binds to human FLT3/FLK2 receptor protein is SEQ ID NO: 13 and an amino acid sequence of a heavy chain of the antigen-binding portion of the antibody or fragment thereof that binds to human FLT3/FLK2 receptor protein is SEQ ID NO: 15.

According to another aspect, the described invention provides a monoclonal antibody or antigen binding fragment thereof, wherein an amino acid sequence of a light chain of an antigen-binding portion of the antibody or fragment thereof that binds to human FLT3/FLK2 receptor protein is SEQ ID NO: 17 and an amino acid sequence of a heavy chain of the antigen-binding portion of the antibody or fragment thereof that binds to human FLT3/FLK2 receptor protein is SEQ ID NO: 19.

According to another aspect, the described invention provides a monoclonal antibody or antigen binding fragment thereof, wherein an amino acid sequence of a light chain of an antigen-binding portion of the antibody or fragment thereof that binds to human FLT3/FLK2 receptor protein is SEQ ID NO: 21, and an amino acid sequence of a heavy chain of the antigen-binding portion of the antibody or fragment thereof that binds to human FLT3/FLK2 receptor protein is SEQ ID NO: 23.

According to another aspect, the described invention provides a monoclonal antibody or antigen binding fragment thereof, wherein an amino acid sequence of a light chain of an antigen-binding portion of the antibody or fragment thereof that binds to human FLT3/FLK2 receptor protein is SEQ ID NO: 25, and an amino acid sequence of a heavy chain of the antigen-binding portion of the antibody or fragment thereof that binds to human FLT3/FLK2 receptor protein is SEQ ID NO: 27.

According to some embodiments, a half maximal effective concentration ($EC_{50}$) of the antibody or fragment thereof is between 1 ng/mL (6.25 pM) and 2,000 ng/mL (12.5 nM). According to some embodiments, the half maximal effective concentration ($EC_{50}$) of the antibody or antigen-binding fragment thereof is between 10 ng/mL (62.5 pM) and 200 ng/mL (1.25 nM). According to some embodiments, FLT3 antibody binding to human FLT3/FLK2 receptor protein on a cell is effective for the cell to internalize the bound antibody or antigen-binding fragment.

BRIEF DESCRIPTION OF THE DRAWINGS

FIGS. 1A and 1B: native fluorescence of amino acids such as phenylalanine, tyrosine and tryptophan. FIG. 1C: measurement of purity of the synthesized antibody.

FIG. 2A: an example of flow cytometry analysis of the peripheral blood of a humanized NOG mouse before (Control; upper row) and three weeks after application of CD3-FLT3 bi-specific antibodies. From left to right: analyses of the amounts of human hCD45+ cells (% of total CD45+ cells), human hCD3+ cells (% of total hCD45+ cells; T-cells), human hCD19+ cells (% of total hCD45+ cells; B-cells), human hCD33+ cells (% of total hCD45+ cells; Myeloid cells). FIG. 2B: effect of bi-specific antibodies administration on the level of chimerism in the peripheral blood in the humanized mice (n=27). FIG. 2C: effect of bi-specific antibodies administration on the levels of T-cells (% hCD3+ cells of total hCD45+ cells), B-cells (% hCD19+ cells of total hCD45+ cells) and myeloid lineages (% hCD33+ cells of total hCD45+ cells) in the peripheral blood (n=27). FIG. 2D: reduced effect of bi-specific antibodies application in a humanized immune-compromised mouse (labeled with asterisks in C) with the reduced amount of human hCD3+ cells (n=3).

FIG. 3A: fluorescence intensity histograms obtained from flow cytometry analysis of supernatants of nine positive hybridoma clones. The supernatants show immune-reactivity against FLT3/FLK2 expressed by REH (human B cell precursor leukemia cells, established from the peripheral blood of a 15 year old girl with ALL at first relapse) cells. A FIG. 3B: a table showing median fluorescence intensity (MFI) of the histograms in FIG. 3A. All nine clones reacted with REH cells that express human FLT3/FLK2 receptor proteins.

FIG. 4A: fluorescence intensity histograms obtained from flow cytometry analysis of purified monoclonal antibodies from nine positive hybridoma clones. The supernatants show immune-reactivity to the human FLT3/FLK2 receptor protein expressed by SP2/0 cells. Monoclonal antibodies were non-reactive with wild-type SP2/0 cells that do not express human FLT3/FL2 receptor protein. FIG. 4B: a table showing median fluorescence intensity (MFI) of the histograms in FIG. 4A. All nine clones reacted with SP2/0 cells that express human FLT3/FLK2 receptor proteins and did not react with wild-type SP2/0 cells.

FIG. 5A: antibody clone Ab2-81. FIG. 5B: antibody clone Abl-23DA. FIG. 5C: antibody clone Ab3-16HA. FIG. 5D: antibody clone Ab0-30A. FIG. 5E: antibody clone Ab1-18New.

DETAILED DESCRIPTION OF THE INVENTION

Glossary

Figure 1A:
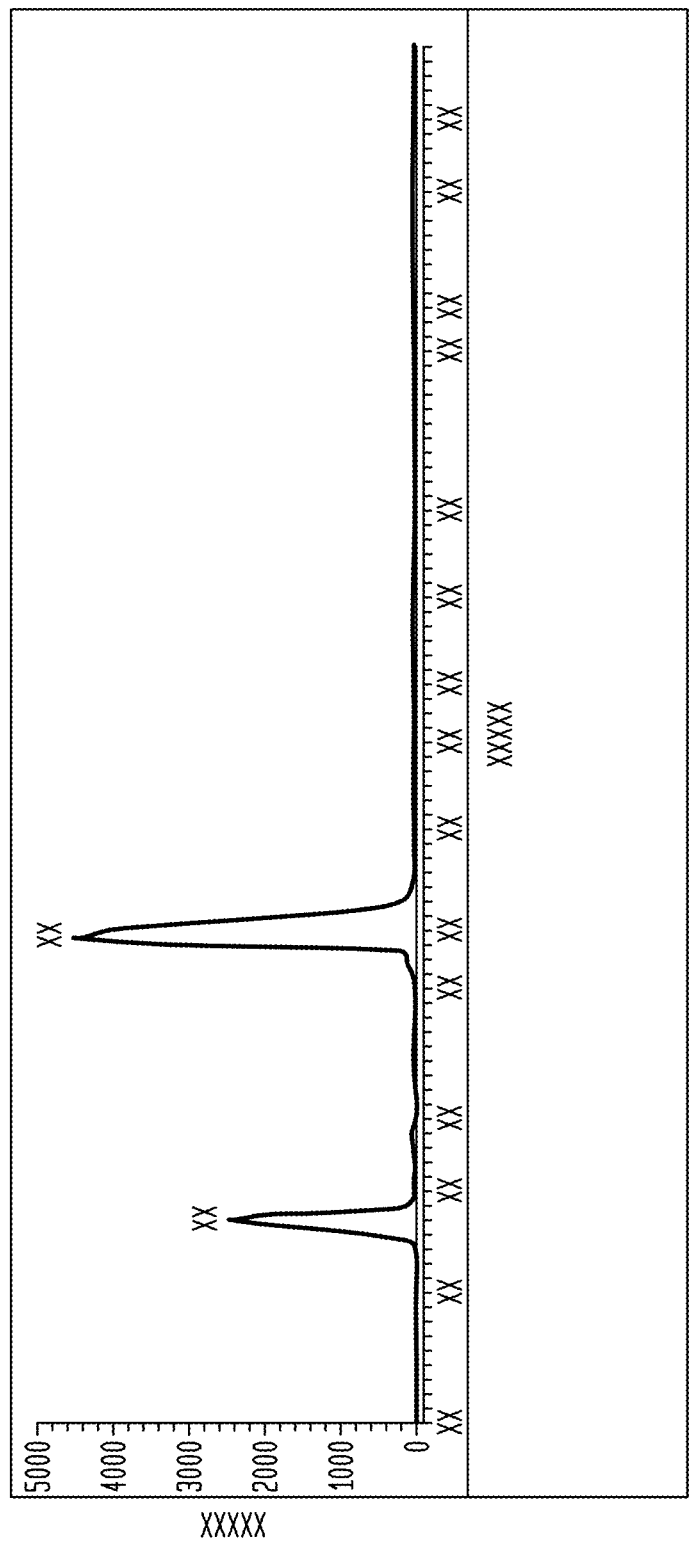
FIGS. 1A, 1B, 1C.

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immmunoglobulins (antibodies). The soluble product of an activated T lymphocyte is lymphokines.

The term "administer" as used herein means to give or to apply. The term "administering" as used herein and its various grammatical forms includes in vivo administration, as well as administration directly to tissue ex vivo.

Antibodies:

Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent 2. Many other species have been found to show two kinds of light chains, but their proportions vary. For example, in the mouse and rat, λ chains comprise but a few percent of the total; in the dog and cat, κ chains are very low;

the horse does not appear to have any κ chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and μ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

An "antigenic determinant" or "epitope" is an antigenic site on a molecule. Sequential antigenic determinants/epitopes essentially are linear chains. In ordered structures, such as helical polymers or proteins, the antigenic determinants/epitopes essentially would be limited regions or patches in or on the surface of the structure involving amino acid side chains from different portions of the molecule which could come close to one another. These are conformational determinants.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, "specificity" means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens "Monoclonal antibodies" (mAbs) can be generated by fusing mouse spleen cells from an immunized donor with a mouse myeloma cell line to yield established mouse hybridoma clones that grow in selective media. A "hybridoma cell" is an immortalized hybrid cell resulting from the in vitro fusion of an antibody-secreting B cell with a myeloma cell. "In vitro immunization", which refers to primary activation of antigen-specific B cells in culture, is another well-established means of producing mouse monoclonal antibodies.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

The term "antibody-dependent cell mediated cytotoxicity (ADCC)" as used herein is triggered when antibody bound to the surface of a cell interacts with Fc receptors on a natural killer (NK) cells. NK cells express the receptor FcγRIII (CD16), which recognizes the IgG1 and IgG3 subclasses. The killing mechanism is analogous to that of cytotoxic T cells, involving the release of cytoplasmic granules containing perforin and granzymes (see below).

CD3 (TCR complex) is a protein complex composed of four distinct chains. In mammals, the complex contains a CD3γ chain, a CD3δ chain, and two CD3ε chains, which associate with the T cell receptor (TCR) and the ζ-chain to generate an activation signal in T lymphocytes. Together, the TCR, the ζ-chain and CD3 molecules comprise the TCR complex. The intracellular tails of CD3 molecules contain a conserved motif known as the immunoreceptor tyrosine-based activation motif (ITAM), which is essential for the signaling capacity of the TCR. Upon phosphorylation of the ITAM, the CD3 chain can bind ZAP70 (zeta associated protein), a kinase involved in the signaling cascade of the T cell.

The term "binding" and its various grammatical forms means a lasting attraction between chemical substances. Binding specificity involves both binding to a specific partner and not binding to other molecules. Functionally important binding may occur at a range of affinities from low to high, and design elements may suppress undesired cross-interactions. Post-translational modifications also can alter the chemistry and structure of interactions. "Promiscuous binding" may involve degrees of structural plasticity, which may result in different subsets of residues being important for binding to different partners. "Relative binding specificity" is a characteristic whereby in a biochemical system a molecule interacts with its targets or partners differentially, thereby impacting them distinctively depending on the identity of individual targets or partners.

The term "contact" and its various grammatical forms as used herein refers to a state or condition of touching or of immediate or local proximity. Contacting a composition to a target destination, such as, but not limited to, an organ, a tissue, or a cell, may occur by any means of administration known to the skilled artisan.

The term "half maximal effective concentration" ($EC_{50}$), as used herein means an antibody concentration that induces a response halfway between the baseline and maximum after an exposure time.

The term "hematopoietic-cell transplantation" (HCT) is used herein to refer to blood and marrow transplantation (BMT), a procedure that involves infusion of cells (hematopoietic stem cells; also called hematopoietic progenitor cells) to reconstitute the hematopoietic system of a patient.

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens. This commitment, which exists before the first contact of the immune system with a given antigen, is expressed by the presence on the lymphocyte's surface membrane of receptors specific for determinants (epitopes) on the antigen. Each lymphocyte possesses a population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions.

Two broad classes of lymphocytes are recognized: the B-lymphocytes (B-cells), which are precursors of antibody-secreting cells, and T-lymphocytes (T-cells), B Lymphocytes B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses. (Paul, W. E., "Chapter 1: The immune system: an introduction," Fundamental Immunology, 4th Edition, Ed. Paul, W. E., Lippicott-Raven Publishers, Philadelphia (1999)).

Cross-linkage dependent B-cell activation requires that the antigen express multiple copies of the epitope complementary to the binding site of the cell surface receptors because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes. (Paul, W. E., "Chapter 1: The immune system: an introduction," Fundamental Immunology, 4th Edition, Ed. Paul, W. E., Lippicott-Raven Publishers, Philadelphia (1999)).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as CD4+ T-cells. The CD4+ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell. (Paul, W. E., "Chapter 1: The immune system: an introduction," Fundamental Immunology, 4th Edition, Ed. Paul, W. E., Lippicott-Raven Publishers, Philadelphia (1999)).

During cognate help for antibody production, the CD40 ligand is transiently expressed on activated CD4+ T helper cells, and it binds to CD40 on the antigen-specific B cells, thereby tranducing a second costimulatory signal. The latter signal is essential for B cell growth and differentiation and for the generation of memory B cells by preventing apoptosis of germinal center B cells that have encountered antigen. Hyperexpression of the CD40 ligand in both B and T cells is implicated in the pathogenic autoantibody production in human SLE patients. (Desai-Mehta, A. et al., "Hyperexpression of CD40 ligand by B and T cells in human lupus and its role in pathogenic autoantibody production," J. Clin. Invest., 97(9): 2063-2073 (1996)).

T-Lymphocytes

T-lymphocytes derive from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on their expression of specific cell surface molecules and the secretion of cytokines. (Paul, W. E., "Chapter 1: The immune system: an introduction," Fundamental Immunology, 4th Edition, Ed. Paul, W. E., Lippicott-Raven Publishers, Philadelphia (1999)).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. Antibody and B-cell receptors evolved to bind to and to protect against microorganisms in extracellular fluids. In contrast, T cells recognize antigens on the surface of other cells and mediate their functions by interacting with, and altering, the behavior of these antigen-presenting cells (APCs). There are three main types of antigen-presenting cells in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an antigen-presenting cell (APC) that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the antigen-presenting cell (APC) for long enough to become activated. ("Chapter 24: The adaptive immune system," Molecular Biology of the Cell, Alberts, B. et al., Garland Science, N Y, 2002).

T-cells are subdivided into two distinct classes based on the cell surface receptors they express. The majority of T cells express T cell receptors (TCR) consisting of α and β chains. A small group of T cells express receptors made of γ and δ chains. Among the α/β T cells are two important sublineages: those that express the coreceptor molecule CD4 (CD4+ T cells); and those that express CD8 (CD8+ T cells). These cells differ in how they recognize antigen and in their effector and regulatory functions.

CD4+ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms.

In addition, T cells particularly CD8+ T cells, can develop into cytotoxic T-lymphocytes (CTLs) capable of efficiently lysing target cells that express antigens recognized by the CTLs. (Paul, W. E., "Chapter 1: The immune system: an introduction," Fundamental Immunology, 4th Edition, Ed. Paul, W. E., Lippicott-Raven Publishers, Philadelphia (1999)).

T cell receptors (TCRs) recognize a complex consisting of a peptide derived by proteolysis of the antigen bound to a specialized groove of a class II or class I MHC protein. The CD4+ T cells recognize only peptide/class II complexes while the CD8+ T cells recognize peptide/class I complexes. (Paul, W. E., "Chapter 1: The immune system: an introduction," Fundamental Immunology, 4th Edition, Ed. Paul, W. E., Lippicott-Raven Publishers, Philadelphia (1999)).

The TCR's ligand (i.e., the peptide/MHC protein complex) is created within antigen-presenting cells (APCs). In general, class II MHC molecules bind peptides derived from proteins that have been taken up by the APC through an endocytic process. These peptide-loaded class II molecules are then expressed on the surface of the cell, where they are available to be bound by CD4+ T cells with TCRs capable of recognizing the expressed cell surface complex. Thus, CD4+ T cells are specialized to react with antigens derived from extracellular sources. (Paul, W. E., "Chapter 1: The immune system: an introduction," Fundamental Immunology, 4th Edition, Ed. Paul, W. E., Lippicott-Raven Publishers, Philadelphia (1999)).

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally nine amino acids in length, are bound into the class I MHC molecules and are brought to the cell surface, where they can be recognized by CD8+ T cells expressing appropriate receptors. This gives the T cell system, particularly CD8+ T cells, the ability to detect cells expressing proteins that are different from, or produced in much larger amounts than, those of cells of the remainder of the organism (e.g., vial antigens) or mutant antigens (such as active oncogene products), even if these proteins in their intact form are neither expressed on the cell surface nor secreted. (Paul, W. E., "Chapter 1: The immune system: an introduction," Fundamental Immunology, 4th Edition, Ed. Paul, W. E., Lippicott-Raven Publishers, Philadelphia (1999)).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. (Paul, W. E., "Chapter 1: The immune system: an introduction," Fundamental Immunology, 4th Edition, Ed. Paul, W. E., Lippicott-Raven Publishers, Philadelphia (1999)).

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching (of the Ig class being expressed) either depend or are enhanced by the actions of T cell-derived cytokines. (Paul, W. E., "Chapter 1: The immune system: an introduction," Fundamental Immunology, 4th Edition, Ed. Paul, W. E., Lippicott-Raven Publishers, Philadelphia (1999)).

CD4+ T cells tend to differentiate into cells that principally secrete the cytokines IL-4, IL-5, IL-6, and IL-10 (TH2 cells) or into cells that mainly produce IL-2, IFN-γ, and lymphotoxin (TH1 cells). The TH2 cells are very effective in helping B-cells develop into antibody-producing cells, whereas the TH1 cells are effective inducers of cellular immune responses, involving enhancement of microbicidal activity of monocytes and macrophages, and consequent increased efficiency in lysing microorganisms in intracellular vesicular compartments. Although the CD4+ T cells with the phenotype of TH2 cells (i.e., IL-4, IL-5, IL-6 and IL-10) are efficient helper cells, TH1 cells also have the capacity to be helpers. (Paul, W. E., "Chapter 1: The immune system: an introduction," Fundamental Immunology, 4th Edition, Ed. Paul, W. E., Lippicott-Raven Publishers, Philadelphia (1999)).

T Cells Involved in Induction of Cellular Immunity

T cells also may act to enhance the capacity of monocytes and macrophages to destroy intracellular microorganisms. In particular, interferon-gamma (IFN-☐) produced by helper T cells enhances several mechanisms through which mononuclear phagocytes destroy intracellular bacteria and parasitism including the generation of nitric oxide and induction of tumor necrosis factor (TNF) production. The TH1 cells are effective in enhancing the microbicidal action because they produce IFN-γ. By contrast, two of the major cytokines produced by TH2 cells, IL-4 and IL-10, block these activities. (Paul, W. E., "Chapter 1: The immune system: an introduction," Fundamental Immunology, 4th Edition, Ed. Paul, W. E., Lippicott-Raven Publishers, Philadelphia (1999)).

Suppressor or Regulatory T (Treg) Cells

A controlled balance between initiation and downregulation of the immune response is important to maintain immune homeostasis. Both apoptosis and T cell anergy (a tolerance mechanism in which the T cells are intrinsically functionally inactivated following an antigen encounter (Scwartz, R. H., "T cell anergy," Annu. Rev. Immunol., 21: 305-334 (2003)) are important mechanisms that contribute to the downregulation of the immune response. A third mechanism is provided by active suppression of activated T cells by suppressor or regulatory CD4+ T (Treg) cells. (Reviewed in Kronenberg, M. et al., "Regulation of immunity by self-reactive T cells," Nature 435: 598-604 (2005)). CD4+ Tregs that constitutively express the IL-2 receptor alpha (IL-2R☐) chain (CD4+CD25+) are a naturally occurring T cell subset that are anergic and suppressive. (Taams, L. S. et al., "Human anergic/suppressive CD4+CD25+ T cells: a highly differentiated and apoptosis-prone population," Eur. J. Immunol., 31: 1122-1131 (2001)). Depletion of CD4+CD25+Tregs results in systemic autoimmune disease in mice. Furthermore, transfer of these Tregs prevents development of autoimmune disease. Human CD4+CD25+ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4+CD25+ T cells can be split into suppressive (CD25high) and nonsuppressive (CD25low) cells, according to the level of CD25 expression. A member of the forkhead family of transcription factors, FOXP3, has been shown to be expressed in murine and human CD4+CD25+ Tregs and appears to be a master gene controlling CD4+CD25+ Treg development. (Battaglia, M. et al., "Rapamycin promotes expansion of functional CD4+ CD25+Foxp3+ regulator T cells of both healthy subjects and type 1 diabetic patients," J. Immunol., 177: 8338-8347 (200)).

Cytotoxic T Lymphocytes (CTL)

The CD8+ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by a series of enzymes produced by activated CTLs, referred to as granzymes. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

Priming

The term "unprimed cells" (also referred to as virgin, naïve, or inexperienced cells) as used herein refers to T cells and B cells that have generated an antigen receptor (TCR for T cells, BCR for B cells) of a particular specificity, but have never encountered the antigen. The term "priming" as used herein refers to the process whereby T cells and B cell precursors encounter the antigen for which they are specific.

For example, before helper T cells and B cells can interact to produce specific antibody, the antigen-specific T cell precursors must be primed. Priming involves several steps: antigen uptake, processing, and cell surface expression bound to class II MHC molecules by an antigen presenting cell, recirculation and antigen-specific trapping of helper T cell precursors in lymphoid tissue, and T cell proliferation and differentiation. Janeway, C A, Jr., "The priming of helper T cells, Semin. Immunol. 1(1): 13-20 (1989). Helper T cells express CD4, but not all CD4 T cells are helper cells. Id. The signals required for clonal expansion of helper T cells differ from those required by other CD4 T cells. The critical antigen-presenting cell for helper T cell priming appears to be a macrophage; and the critical second signal for helper T cell growth is the macrophage product interleukin 1 (IL-1). Id. If the primed T cells and/or B cells receive a second, co-stimulatory signal, they become activated T cells or B cells.

The term "transplantation" as used herein, refers to removal and transfer of cells, a tissue or an organ from one part or individual to another.

According to one aspect, the described invention provides a recombinant bispecific antibody that binds to both human Flt3 and human CD3. According to some embodiments, the Flt3 antibody binds to a FLT3/FLK2 receptor protein. According to some embodiments, the FLT3/FLK2 receptor protein is a mammalian protein. According to some embodiments, the FLT3/FLK2 receptor protein is human. According to some embodiments, the FLT3/FLK2 receptor protein is native. According to some embodiments, the FLT3/FLK2 receptor protein is in a modified form. According to some embodiments, the FLT3/FLK2 receptor protein is in a denatured form. According to some embodiments, the FLT3/FLK2 receptor protein is in an unmodified form. According to some embodiments, the Flt3 antibody is selected from the group consisting of a monoclonal antibody, a polyclonal antibody, an antibody fragment and a synthetic antibody mimic. According to some embodiments, the Flt3 antibody is a monoclonal antibody. According to some embodiments, the FLt3 monoclonal antibody is selected from the group consisting of a synthetic antibody and an engineered antibody. According to some embodiments, the synthetic antibody is a recombinant antibody. According to some embodiments, the recombinant antibody is a single-chain variable fragment (scFv) antibody. According to some embodiments, the single chain antibody comprises a C terminus of an Fab fragment of an Flt3 antibody that is joined to a CH2 domain of an IgG1. According to some embodiments, the CH2 domain of IgG1 is joined to a single chain variable fragment (ScFv) of an antibody that reacts with a subunit of human CD3. According to some embodiments, the single chain variable fragment is a monoclonal antibody. According to some embodiments, the subunit of human CD3 is UCHT1. According to some embodiments, the engineered antibody is a chimeric antibody. According to some embodiments, the engineered antibody is a humanized antibody.

According to some embodiments, the FLT3 antibody binding to Flt3 is effective to block the binding of an FLT3 ligand to FLT3/FLK2 receptor protein. According to some embodiments, the FLT3 antibody binding to Flt3 on the cell is effective for the cell to internalize the bound antibody.

According to some embodiments, the Flt3 antibody has a half maximal effective concentration ($EC_{50}$) between about 1 ng/mL (6.25 pM) and about 2,000 ng/mL (12.5 nM). According to some embodiments, the Flt3 antibody has a half maximal effective concentration ($EC_{50}$) between about 10 ng/mL (62.5 pM) and about 200 ng/mL (1.25 nM). According to some embodiments, the bispecific antibody that binds to both human Flt3 and human CD3 is effective to eliminate one or more of hematopoietic stem cells (HPC), early hematopoietic progenitors (HP), and cancer cells. According to some embodiments, one or more of the HPC, HP, and cancer cells express FLT3. According to some embodiments, a subject in need thereof is a patient that qualifies for, will be receiving or is receiving BM/HPCPC transplantation. Examples of the cancer cells include, without limitation, blast cells of acute myeloid leukemia (AML), acute lymphocytic leukemia (ALL), blast-crisis phase of chronic myeloid leukemia (BC-CML) and chronic lymphocytic leukemia (CLL). According to some embodiments, the bispecific antibody is effective to condition patients undergoing bone marrow (BM)/hematopoietic stem cell (HSC) transplantation. According to some embodiments, the HSC/HP transplantation is for treating a hematological malignancy or hyperproliferative disorder, e.g., Acute Myeloid Leukemia (AML), Acute Lymphoblastic Leukemia (ALL), Chronic Lymphocytic Leukemia (CLL), Chronic Myeloid Leukemia (CML), peripheral T cell lymphoma, follicular lymphoma, diffuse large B cell lymphoma, Hodgkin lymphoma, non-Hodgkin lymphoma, neuroblastoma, non-malignant inherited and acquired marrow disorders (e.g. sickle cell anemia, beta-thalassemia major, refractory Diamond-Blackfan anemia, myelodysplastic syndrome, idiopathic severe aplastic anemia, paroxysmal nocturnal hemoglobinuria, pure red cell aplasia, Fanconi anemia, amegakaryocytosis, or congenital thrombocytopenia), multiple myeloma, or Severe Combined Immunodeficiency (SCID).

According to another aspect, a method for preparing a recombinant single chain bi-specific antibody that binds to both human FLT3 and human CD3 comprises joining a C-terminus of an Fab fragment of an Flt3 monoclonal antibody to a CH2 domain of IgG1, and joining to the CH2 domain of the IgG1 a single chain variable fragment (ScFv) of a monoclonal antibody that reacts with a subunit of human CD3 (UCHT1).

According to another aspect, the described invention provides for a method of eliminating hematopoietic stem cells/hematopoietic progenitors (HSC/HP) in patients in need thereof. According to some embodiments, the method comprises administering to said patients a bi-specific antibody that specifically binds to HSC/HP and to T-cells. Specifically, the bi-specific antibody binds to human FLT3 expressed by HSC/HP and to human CD3 expressed by T cells. The simultaneous binding of the antibody redirects T-cells to specifically eliminating the HSC/HP of the patients.

The method provides also the administration of an effective amount of the specific antibody to the patient. The effective amount goes from 0.01 mg/kg to 10 mg/kg, better 0.05 mg/kg to 2 mg/kg, better 0.1 mg/kg to 0.5 mg/kg, better 0.1 mg/kg to 0.3 mg/kg, better 0.1 mg/kg.

According to some embodiments, the bi-specific antibody that binds to primate and human CD3 is a humanized antibody.

According to some embodiments, the bi-specific antibody or antigen-binding portion thereof comprises amino acid sequences of FLT3 antibody.

According to some embodiments, the bi-specific antibody or antigen-binding portion thereof comprises amino acid sequences of CD3 antibody.

According to some embodiments, the bi-specific antibody or antigen-binding portion thereof comprises an isotype selected from the group consisting of: an immunoglobulin G (IgG), an IgM, an IgE, an IgA, or an IgD isotype.

According to another aspect, the invention also provides for a method of eliminating HSC/HP in a patient in need thereof, wherein the HSC/HP express FLT3. The method comprises selecting a patient in need of eliminating HSC/HP and administering to the patient a therapeutically effective amount of a pharmaceutical composition comprising a bi-specific antibody specifically binding to human FLT3 expressed by HSC/HP and to human CD3 expressed by T-cells, wherein the bi-specific antibody redirects T-cells to kill HSC/HP of the patient.

The patients in need of eliminating HSC/HP are patients suffering from Acute Myeloid Leukemia (AML), Acute Lymphoblastic Leukemia (ALL), Chronic Lymphocytic Leukemia (CLL), Chronic Myeloid Leukemia (CML), peripheral T cell lymphoma, follicular lymphoma, diffuse large B cell lymphoma, Hodgkin lymphoma, non-Hodgkin lymphoma, non-hematological malignancies such as neuroblastoma, non-malignant inherited and acquired marrow disorders (e.g. sickle cell anemia, beta-thalassemia major, refractory Diamond-Blackfan anemia, myelodysplastic syndrome, idiopathic severe aplastic anemia, paroxysmal nocturnal hemoglobinuria, pure red cell aplasia, Fanconi anemia, amegakaryocytosis, or congenital thrombocytopenia), multiple myeloma, Severe Combined Immunodeficiency (SCID) and other disorders that are treated using Bone Marrow (BM)/Hematopoietic Stem Cell (HSC) transplantation.

The pharmaceutical composition comprises the antibody and pharmaceutically acceptable carriers, diluents or excipients. The carriers are selected from for example, one or more of water, saline, phosphate buffered saline, dextrose, glycerol, ethanol and the like, as well as combinations thereof. Pharmaceutically acceptable carriers can further comprise minor amounts of auxiliary substances such as wetting or emulsifying agents, preservatives or buffers, which enhance the shelf life or effectiveness of the binding proteins. The pharmaceutical compositions can, as is well known in the art, be formulated so as to provide rapid, sustained or delayed release of the active ingredient after administration (Mishra, M. K. (2016). *Handbook of encapsulation and controlled release*. Boca Raton, CRC Press, Taylor & Francis Group, CRC Press is an imprint of the Taylor & Francis Group, an Informa business, incorporated herein by reference in its entirety).

The pharmaceutical composition may further comprise another component such as T-cells or an antitumor agent. Antitumor agents administered in conjunction with the antibody include any agents which destroy or damage a tumor or malignant cells.

The antitumor agent is selected from the group consisting of suitable anti-neoplastic agents that are known to those skilled in the art and include anthracyclines (e.g. daunomycin and doxorubicin), auristatin, methotrexate (MTX), vindesine, neocarzinostatin, cis-platinum, chlorambucil, cytosine arabinoside, 5-fluorouridine, melphalan, ricin and calicheamicin including combination chemotherapy such with doxorubicin, bleomycin, vinblastine, and dacarbazine (ABVD), BEACOPP or escalated BEACOPP (bleomycin, etoposide, doxorubicin, cyclophosphamide, vincristine, procarbazine, and prednisone) and Stanford V (doxorubicin, vinblastine, mechlorethamine, vincristine, bleomycin, etoposide, and prednisone). The antitumor agent can also be immunotherapy (e.g. anti-CD20 antibody rituximab), immunotoxins (e.g. Brentuximab vedotin (SGN-35) is an immunotoxin comprised of a CD-30 directed antibody linked to the antitubulin agent monomethyl auristatin E (MMAE)), adoptive immunotherapy (cytotoxic T lymphocytes), programmed death 1 (PD-1) blockade (eg, nivolumab, pembrolizumab).

According to another aspect, the invention further provides for a method of testing of bi-specific antibodies redirecting T-cells to kill HSC/HP in an animal model in vivo, wherein said animal model is immune-compromised humanized mice with a chimeric mouse-human hematopoietic system, wherein said humanized mice are created by transplantation of human HSC/HP or transplantation of human post-natal hemogenic endothelial cells into said myeloablated immune-compromised mice.

The bi-specific antibody of the present invention has been synthesized according to the method described in Durben et al. (Molecular Therapy, vol. 23, no. 4 Apr. 2015), which is incorporated herein by reference in its entirety.

The FLT3 antibody sequence used is described in the U.S. Pat. No. 9,023,996 to Grosse-Hovest et al, also incorporated herein by reference in its entirety.

It is to be understood that while the invention is described in conjunction of the preferred embodiments thereof, those skilled in the art are aware that other embodiments could be made without departing from the spirit of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

To better illustrate the invention the following examples are given.

Example 1: Antibody Synthesis Description

Background Information

Fabsc is a recombinant bispecific antibody format. The Fabsc format for a bispecific antibody targeting FLT3 (using 4G8 clone) and CD3 (using UCHT1 antibody sequence, also referred to as huxCD3v1) is as follows: C-terminus of Fab fragment of Flt3 mAb will be joined to the CH2 domain of IgG1, followed by the ScFv of UCHT1.

Sequences of 4G8 clone and UCHT1 were obtained from U.S. Pat. Nos. 9,023,996 B2 and 6,054,297, respectively, incorporated herein by reference in their entirety.

Scope of Experiment

Gene synthesis of 4G8 and UCHT1 variable heavy and light chain sequences based on the format described in the background.

Molecular construction of IgG expression vectors.

0.1 liter premium transient production in HEK293 cells.

Custom purification (KappaSelect and protein L-columns and eluted at pH 2.3).

Protein aggregation analysis by SE-HPLC.

Target Deliverables

All purified protein from 0.1 liter production.

Study Report including: Certificate of Analysis, CE-SDS analysis, SE-HPLC analysis report.

Depending on yield obtained after expression and purification, client will determine if produced antibody is to be used for the following analytical steps:

Test purity, monomer content, and aggregation by SE-HPLC (0.1 mg).

Association and dissociation using varying concentrations of antigen and calculation of kD by ForeBio Octet QKe (0.2 mg).

Results

The Fabsc antibody was cloned into a high expression mammalian vector system and a small-scale (0.1 liter) premium transient production was completed in HEK293 cells. The protein was purified by Protein L purification and 20.17 mg of protein was obtained. Yields were reported and client confirmed that SE-HPLC should be performed. The antibody was determined to be 92% non-aggregated monomer by SE-HPLC.

Vector Construction and Transient Production

Molecular Construction of Expression Vector

DNA Studio gene synthesized and cloned programmed sequences into one of high expression mammalian vectors. Completed constructs were sequence confirmed before proceeding to transfection.

TABLE A

| Construct Name | Fabsc HC | Fabsc LC |
|---|---|---|
| Internal code | H3113 | L3113 |
| Antibody details | Human IgG1 Fab | Human kappa |
| Notes | Sequences were codon optimized | |

Small-Scale Transient Transfection

HEK293 cells were seeded in a shake flask one day before transfection, and were grown using serum-free chemically defined media. The DNA expression constructs were transiently transfected into 0.1 liter of suspension HEK293 cells using standard operating procedure for transient transfection. After 20 hours, cells were sampled to obtain the viability and viable cell count, and titer was measured (Octet QKe, ForteBio). The culture was harvested at day 5 and additional readings were taken.

Protein L Affinity Purification

Figure 1B:
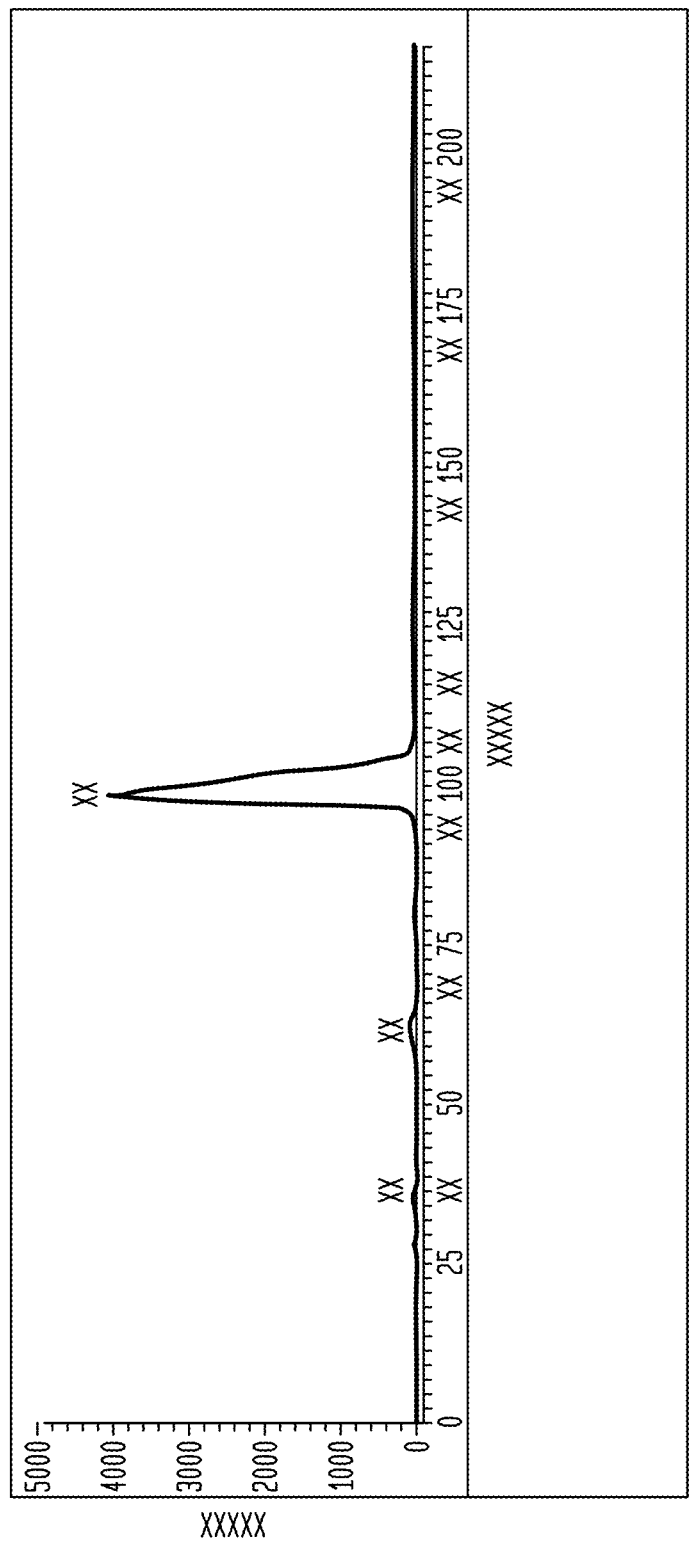

The conditioned media for Fabsc was harvested and clarified from the transient transfection production run by centrifugation and filtration. The supernatant was run over a Protein L column and eluted with a low pH buffer. Filtration using a 0.2 µm membrane filter was performed before aliquoting. After purification and filtration, the protein concentration was calculated from the OD280 and the extinction coefficient. See Table 1 for a summary of yields and aliquots. CE-SDS analysis was performed (LabChip GXII, Perkin Elmer) and the electropherogram was plotted and is shown in FIGS. 1A and 1B.

SE-HPLC Analysis

Figure 1C:
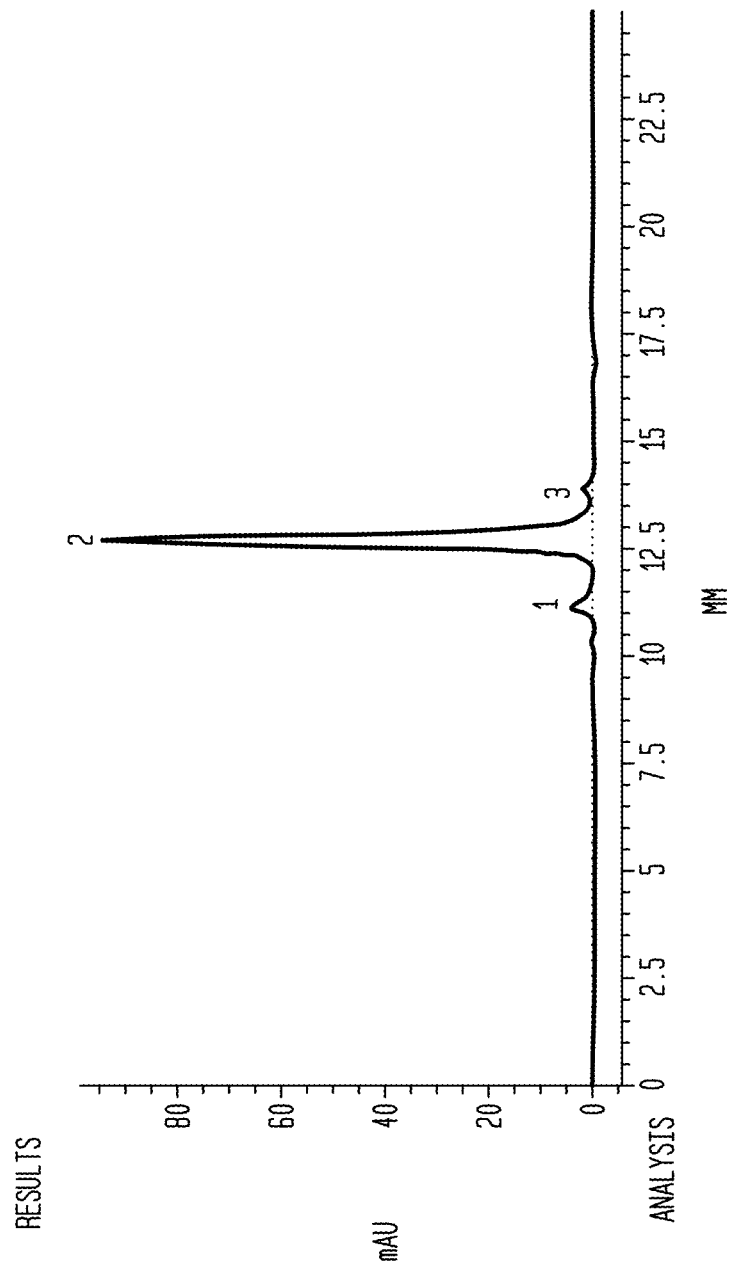
Figure 2A:
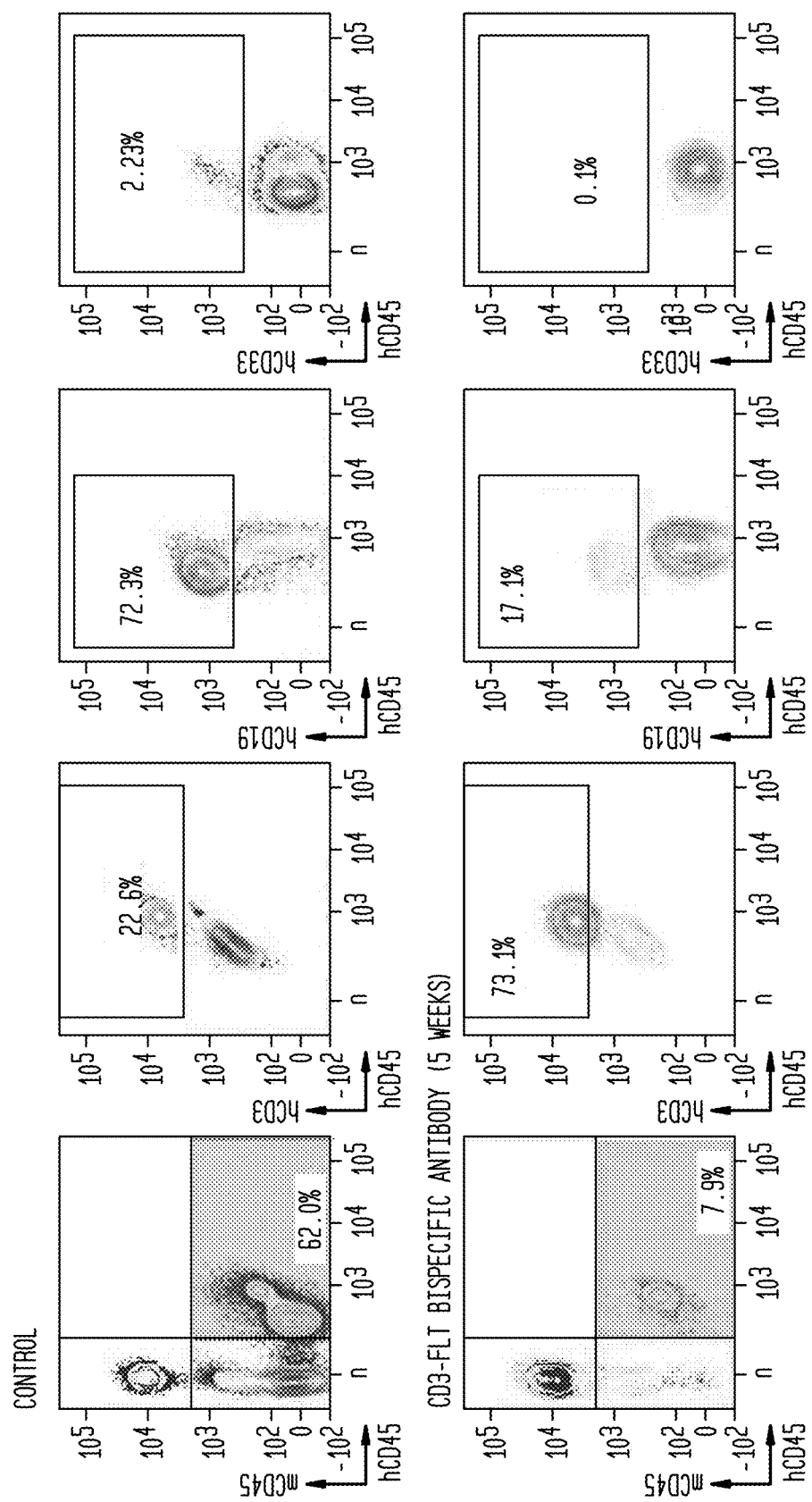
FIGS. 2A, 2B, 2C, 2D. Administering bi-specific antibodies that bind to FLT3/FLK2 expressed by HSC/HP and CD3 expressed by T-cells reduces the level of chimerism in the peripheral blood in the humanized immune-compromised mice.
Figure 2C:
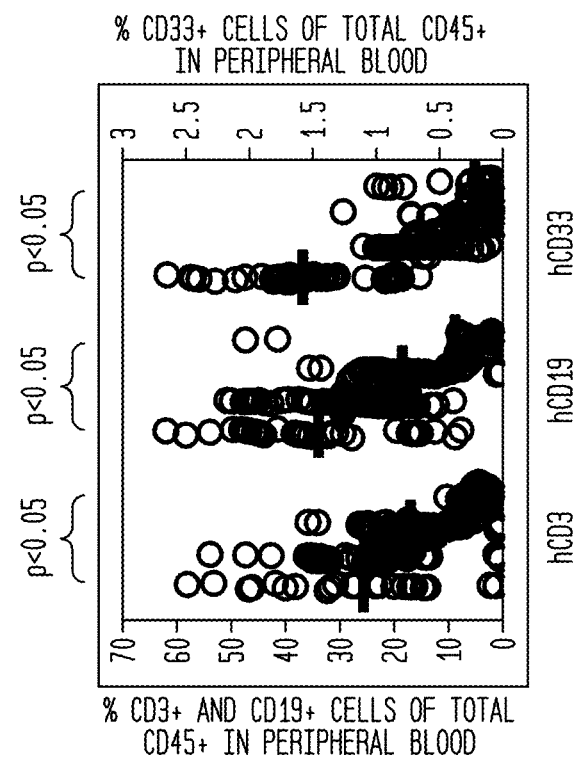
Figure 2B:
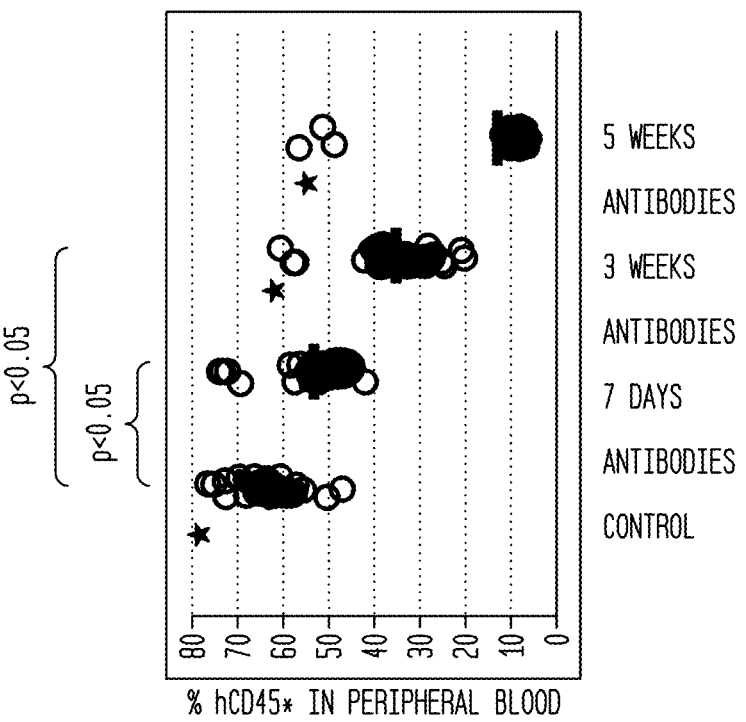
Figure 2D:
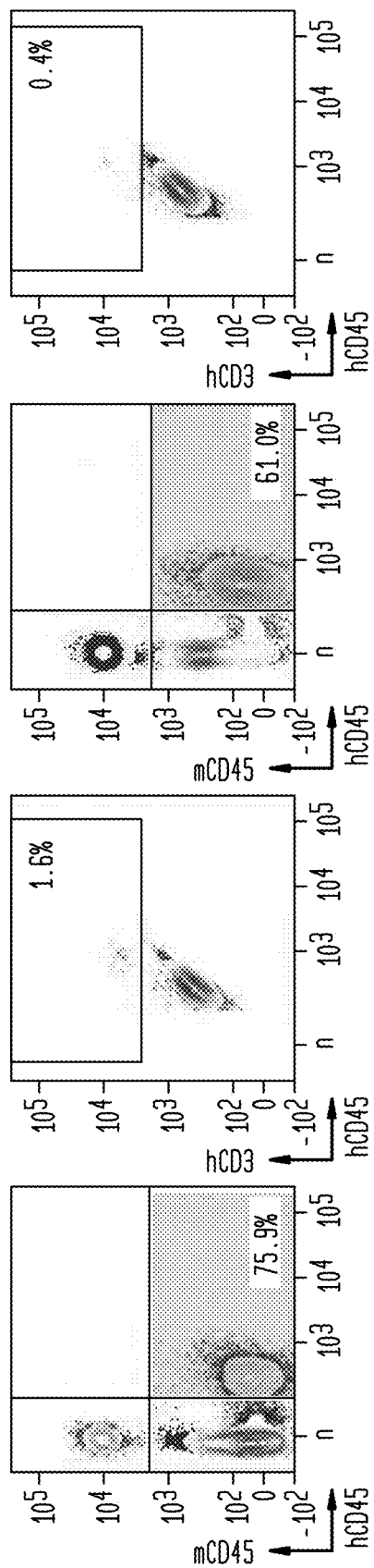

5 µL of purified antibody was injected into a MAbPac SEC-1, 5 µm, 4×300 mm column with a flow of 0.2 mL/min for 25 minutes. The protein eluted at the expected time with 92% in its non-aggregated form. The chromatogram and specifications of the SE-HPLC can be reviewed in FIG. 1C.

See Table 1 for a summary of aggregation level.

TABLE 1

Final yields and aliquots

| Protein Name | Lot # | HC# | LC# | Conc. (mg/mL) | Vol. (mL) | No. of Vials | Total Yield (mg) | SE-HPLC analysis (% monomeric) |
|---|---|---|---|---|---|---|---|---|
| Fabsc | 4622-848799 | H3113 | L3113 | 5.45 | 0.5 | 7 | 19.07 | >92 |
|  | 4622-848799 |  |  |  | 0.2 | 1 | 1.09 |  |

Project Summary

The Fabsc antibody was cloned into LakePharma's high expression mammalian vector system and a small-scale (0.1 liter) premium transient production was completed in HEK293 cells. The protein was purified by Protein L purification and 20.17 mg of protein was obtained and 19.07 mg was delivered. The antibody was determined to be 92% non-aggregated by SE-HPLC. See Table 1 for a summary of yields and aliquots.

Protein Purification Results
Process Summary and Specifications
Protein L affinity chromatography
0.2 µm sterile filtering

TABLE 2

| | |
|---|---|
| Protein Name | Fabsc |
| Lot # | 4622-848799 |
| Extinction Coefficient (used for concentration calculation) | 1.67 mg/ml$^{-1}$ cm$^{-1}$ |
| Protein concentration | 5.45 mg/ml |
| Volume | 0.50 ml |
| Total Protein | 2.72 mg |
| Endotoxin | Not Measured |
| Physical state | Liquid |
| Buffer | 230 mM HEPES, 115 mM NaCl, 58 mM naOAc, pH 7.0 |

TABLE 3

| | |
|---|---|
| Test | SE-HPLC |
| SR # | 3916 |
| Sample ID | Fabsc (PP4622) |
| Date | 2015 Dec. 9 |
| Scientist | SW |

Methods

TABLE 4

| Peak # | Time (min) | Peak Size (kDa) | Peak Area % | Peak ID |
|---|---|---|---|---|
| 1 | 11.2 | ~230 | 5.8 | Aggregate |
| 2 | 12.7 | ~100 | 91.8 | Monomer |
| 3 | 13.9 | ~40 | 2.4 | Fragment |
| 4 |  |  |  |  |
| 5 |  |  |  |  |
| 6 |  |  |  |  |

TABLE 5

| | |
|---|---|
| Column | MabPac SEC-1, 5 µm, 4 × 300 mm |
| Mobile Phase | 50 mM Sodium Phosphate, 300 mM NaCl, pH 6.2 |
| Isocratic | 0-25 min |
| Flow Rate (mL/min) | 0.2 |
| Injection Volume (µL) | 5 |

Example 2: Preparation or Conditioning of a Patient for Bone Marrow/Hematopoietic Stem Cell (BM/HSC) Transplant Preparation or conditioning of a patient for bone marrow/hematopoietic stem cell (BM/HSC) transplant is a critical element of the procedure. It serves two main purposes: (1) It provides adequate immunosuppression of the patient and clears sufficient niche space in the bone marrow for the transplanted HSC. This allows transplanted cells to engraft in the recipient; (2) It often helps to eradicate the source of malignancy.

Conditioning of patients has traditionally been achieved by administering maximally tolerated doses of a cocktail of chemotherapeutical agents with or without radiation. Components of the cocktail are often chosen to have non-overlapping toxicities. All preparative regiments that are currently in use are toxic and have severe side effects that can be life threatening. Among these side effects are mucositis, nausea and vomiting, alopecia, diarrhea, rash, peripheral neuropathies, infertility, pulmonary and hepatic toxicities. Many of these side effects are especially dangerous for older and sick patients and often become a decisive component in deciding whether a patient will receive a transplant.

To eliminate use of chemotherapeutic agents for conditioning of the patients undergoing BM/HSC transplantations we developed a method of selective elimination of hematopoietic stem cells/hematopoietic progenitors (HSC/HP) using redirected T-cell killing. This method is based on the use of bi-specific antibodies that bind to a target (FLT3) on the surface of HSC/HP and also to a target (CD3) on a surface of T-cells, recruiting T-cells against HSC/HP.

As a proof of principle that the developed method is useful for eliminating HSC/HP we tested bi-specific (FLT3xCD3) antibodies designed for killing of leukemic blasts in primary peripheral blood mononuclear cells of acute myeloid leukemia (AML) patients (Durben, Schmiedel et al. 2015).

Females (4-6 weeks of age) of immune-compromised NOG (NOD.Cg-Prkdcscid Il2rgtml Sug/JicTac) mice were used for transplantation of human CD34+ HSC/HP from umbilical cord blood (CB). Mononuclear cell fraction of CB was separated using Ficoll-Paque (GE Healthcare Life Sciences) by gradient density centrifugation. Briefly, CB treated with anti-coagulant was mixed with phosphate-buffered saline (PBS) in the 1:1 ratio and overlaid (35 ml of the mixture) on a layer of Ficoll-Paque (10 ml) in 50 ml conical centrifuge tubes. The tubes were then spun at a speed of 400×g. A monocyte lymphocyte layer was carefully removed and cells obtained from that layer were washed twice with PBS.

CD34+ HSC/HP were isolated by negative selection with platelet depletion (Stemcell Technologies). Unwanted cells were targeted for removal with Tetrameric Antibody Complexes recognizing CD2, CD3, CD11b, CD11c, CD14, CD16, CD19, CD24, CD56, CD61, CD66b, glycophorin A and dextran-coated magnetic particles. The labeled cells were separated using an EasySep™ magnet without the use of columns.

CD34+ HSC/HP were re-suspended in PBS at 10,000-50,000 cells per 200 µl for transplantation into a myeloablated NOG mouse.

Mice were myeloablated using Busulfan (10 mg/kg) via intra-peritoneal injection twenty-four hours before the transplantation. CD34$^+$ HSC/HP were transplanted by tail vein injection of 200 µl of cell suspension (n=52). Eighteen (18) weeks post-transplantation peripheral blood of transplanted mice was tested for the presence of human CD45$^+$ cells. Mice with the level of chimerism 40% (% of human CD45$^+$ cells≥40% of total CD45$^+$ cells) were selected for further experimentation (n=27; FIG. 1A, FIG. 1B). The level of chimerism was tested in the peripheral blood and calculated as follows:

$$\frac{\% \ hCD45^+}{\% \ hCD45^+ + \% \ mCD45^+} * 100\%$$

Peripheral blood of the selected mice was also tested for the presence of human B-cells (hCD19$^+$), human T-cells (hCD3$^+$) and human cells belonging to myeloid lineages (hCD33$^+$). A majority of mice exhibited robust development of all three lineages (FIG. 1A, FIG. 1B). Some mice (n=3) were deficient for the development of CD3$^+$ cells (FIG. 1B asterisks, FIG. 1D). These T-cell deficient mice were used as an internal control group within the experiment.

Protein Sequence of Insert

Fabsc HC [H3113](SEQ ID NO: 1):
MEWSWVFLFFLSVTTGVHSQVQLQQPGAELVKPGASLKLSCKSSGYTFTS
YWMHWVRQRPGHGLEWIGEIDPSDSYKDYNQKFKDKATLTVDRSSNTAYM
HLSSLTSDDSAVYYCARAITTTPFDFWGQGTTLTVSSASTKGPSVFPLAP
SSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTSPPSP
APPVAGPSVFLEPPKPKDTLMISRTPEVTCVVVGVSHEDPEVKFNWYVDG
VEVHNAKTKPREEQYQSTYRVVSVLTVLHQDWLNGKEYKCKVSNKQLPSP
IEKTISKAKGGGGAGGGGEVQLVESGGGLVQPGGSLRLSCAASGYSFTGY
TMNWVRQAPGKGLEWVALINPYKGVTTYADSVKGRFTISVDKSKNTAYLQ
MNSLRAEDTAVYYCARSGYYGDSDWYFDVWGQGTLVTVSSGGGGSGGGGS
GGGGSDIQMTQSPSSLSASVGDRVTITCRASQDIRNYLNWYQQKPGKAPK
LLIYYTSRTFSGVPSRFSGSGSGTDYTLTISSLQPEDFATYYCQQGNTLP
WTFGQGTKVEIKR*

Fabsc LC [L3113](SEQ ID NO: 2):
METDTLLLWVLLLWVPGSTGDIVLTQSPATLSVTPGDSVSLSCRASQSIS
NNLHWYQQKSHESPRLLIKYASQSISGIPSRFSGSGSGTDFTLSINSVET
EDFGVYFCQQSNTWPYTFGGGTKLEIKRTVAAPSVFIFPPSDEQLKSGTA
SVVCLLNNFYPREAKVQWKVDNALQSGNSQESVIEQDSKDSTYSLSSTLT
LSKADYEKHKVYACEVTHQGLSSPVTKSFNR GEC*

Signal Peptide
Variable heavy
Variable light
DNA Sequence of Insert

Fabsc HC [H3113](SEQ ID NO: 3):
ATGGAATGGAGCTGGGTCTTTCTCTTCTTCCTGTCAGTAACGACTGGTGT
CCACTCCCAGGTGCAGCTGCAGCAGCCTGGTGCCGAGCTCGTGAAACCTG
GCGCCTCCCTGAAGCTGTCCTGCAAGTCCTCCGGCTACACCTTCACCAGC
TACTGGATGCACTGGGTGCGACAGAGGCCTGGCCACGGACTGGAATGGAT
CGGCGAGATCGACCCCTCCGACTCCTACAAGGACTACAACCAGAAGTTCA
AGGACAAGGCCACCCTGACCGTGGACAGATCCTCCAACACCGCCTACATG
CACCTGTCCTCCCTGACCTCCGACGACTCCGCCGTGTACTACTGCGCCAG
AGCCATCACAACCACCCCCTTCGATTTCTGGGGCCAGGGCACCACACTGA
CAGTGTCCTCCGCTTCCACCAAGGGCCCCTCCGTGTTTCCTCTGGCCCCT
TCCAGCAAGTCCACCTCTGGCGGAACAGCCGCTCTGGGCTGCCTCGTGAA
GGACTACTTCCCCGAGCCTGTGACCGTGTCCTGGAACTCTGGCGCTCTGA
CATCCGGCGTGCACACCTTCCCTGCTGTGCTGCAGTCTAGCGGCCTGTAC
TCCCTGTCCAGCGTCGTGACCGTGCCTTCCAGCTCTCTGGGCACCCAGAC
CTACATCTGCAACGTGAACCACAAGCCTTCCAACACCAAGGTGGACAAGA
AGGTGGAACCCAAGTCCTGCGACAAGACCCACACCAGCCCTCCAAGCCCT

```
GCTCCTCCTGTGGCTGGCCCTAGCGTGTTCCTGTTCCCTCCAAAGCCCAA

GGATACCCTGATGATCTCCCGGACCCCCGAAGTGACCTGCGTGGTCGTGG

GAGTGTCTCACGAGGACCCTGAAGTGAAGTTCAATTGGTACGTGGACGGC

GTGGAAGTGCACAACGCCAAGACCAAGCCTAGAGAGGAACAGTACCAGTC

CACCTACCGGGTGGTGTCCGTGCTGACCGTGCTGCACCAGGATTGGCTGA

ACGGCAAAGAGTACAAGTGCAAGGTGTCCAACAAGCAGCTGCCCAGCCCC

ATCGAAAAGACCATCTCCAAGGCTAAGGGCGGAGGCGGAGCTGGTGGTGG

CGGAGAAGTGCAGCTGGTGGAATCTGGCGGCGGACTGGTGCAGCCTGGCG

GATCTCTGAGACTGTCTTGTGCCGCCAGCGGCTACTCTTTCACCGGCTAT

ACCATGAATTGGGTGCGCCAGGCCCCTGGAAAGGGCCTGGAATGGGTGGC

CCTGATCAACCCCTACAAGGGCGTGACCACCTACGCCGACTCCGTGAAGG

GCCGGTTCACCATCTCCGTGGACAAGTCCAAGAATACCGCTTACCTGCAG

ATGAACTCCCTGCGGGCCGAGGACACCGCTGTGTATTACTGTGCTAGATC

CGGCTACTACGGCGACAGCGATTGGTACTTCGACGTGTGGGGACAGGGAA

CCCTCGTGACTGTGTCATCAGGCGGCGGTGGTTCTGGCGGAGGGGGATCT

GGGGGCGGTGGATCCGATATCCAGATGACCCAGTCCCCCAGCTCCCTGTC

TGCCTCTGTGGGCGACAGAGTGACCATCACCTGTCGGGCCTCTCAGGACA

TCCGGAACTACCTGAACTGGTATCAGCAGAAGCCCGGCAAGGCCCCCAAG

CTGCTGATCTACTACACCTCCCGGCTGGAAAGCGGCGTGCCCTCCAGATT

CTCCGGCTCTGGCTCTGGAACCGACTATACCCTGACCATCTCTAGCCTGC

AGCCCGAGGACTTCGCCACCTACTACTGCCAGCAGGGCAACACCCTGCCC

TGGACCTTTGGCCAGGGAACAAAGGTGGAAATCAAGCGGTGA

Fabsc LC [L3113] (SEQ ID NO: 4):
ATGGAGACCGACACCCTGCTGCTCTGGGTGCTGCTGCTCTGGGTGCCCGG

CTCCACCGGAGACATCGTGCTGACCCAGTCTCCCGCCACCCTGTCTGTGA

CCCCTGGCGACTCTGTGTCCCTGTCCTGCAGAGCCTCCCAGTCCATCTCC

AACAACCTGCACTGGTATCAGCAGAAGTCCCACGAGAGCCCTCGGCTGCT

GATTAAGTACGCCAGCCAGTCTATCTCCGGCATCCCCTCCAGATTCTCCG

GCTCTGGCTCTGGCACCGACTTCACCCTGTCCATCAACTCCGTGGAAACC

GAGGACTTCGGCGTGTACTTCTGCCAGCAGTCCAACACCTGGCCCTACAC

CTTTGGCGGAGGCACCAAGCTGGAAATCAAGCGGACCGTGGCCGCCCCA

GCGTGTTCATCTTCCCTCCCAGCGACGAGCAGCTGAAGTCTGGCACCGCC

AGCGTGGTGTGCCTGCTGAACAACTTCTACCCCGCGAGGCCAAGGTGCA
```

```
GTGGAAGGTGGACAACGCCCTGCAGAGCGGCAACAGCCAGGAGAGCGTGA

CCGAGCAGGACTCCAAGGACAGCACCTACAGCCTGAGCAGCACCCTGACC

CTGAGCAAGGCCGACTACGAGAAGCACAAGGTGTACGCCTGCGAGGTGAC

CCACCAGGGACTGTCTAGCCCCGTGACCAAGAGCTTCAACCGG GGCGAG

TGCTAA
```

Example 3: Generation and Characterization of Monoclonal Antibodies Directed Against Flt3/FLK2 Human Receptor Protein Cells from the murine myeloma cell line SP2/0 were transduced with lentivirus expressing full coding sequence of human FT3/FLK2 receptor protein and a selection marker for puromycin resistance. Transduced cells were selected in the presence of puromycin in vitro. Cells selected and verified for expression of the human FLT3/FLK2 protein cells (SP2/0-Hu-FLT3) were used as antigen.

Eight week-old Balb/c mice were immunized three times with 107 SP2/0-Hu-FLT3 cells by intraperitoneal injection every 5 days in order to generate antibodies specific to FLT3/FLK2 protein. The development of antibodies was tested by screening blood serum of the immunized mice for binding of the FLT3/FLK2 antigen using flow cytometry.

Figures 3A, 3B:
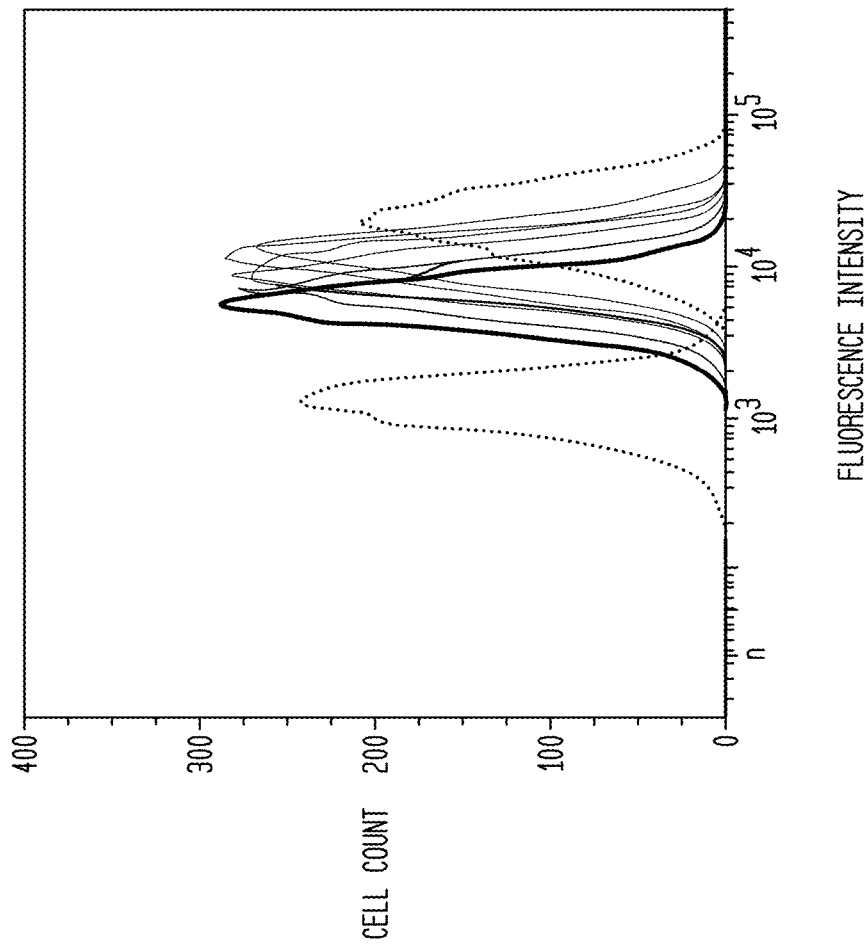
FIGS. 3A and 3B. Screening of culture supernatants from clonally expanded hybridomas.
Figures 4A, 4B:
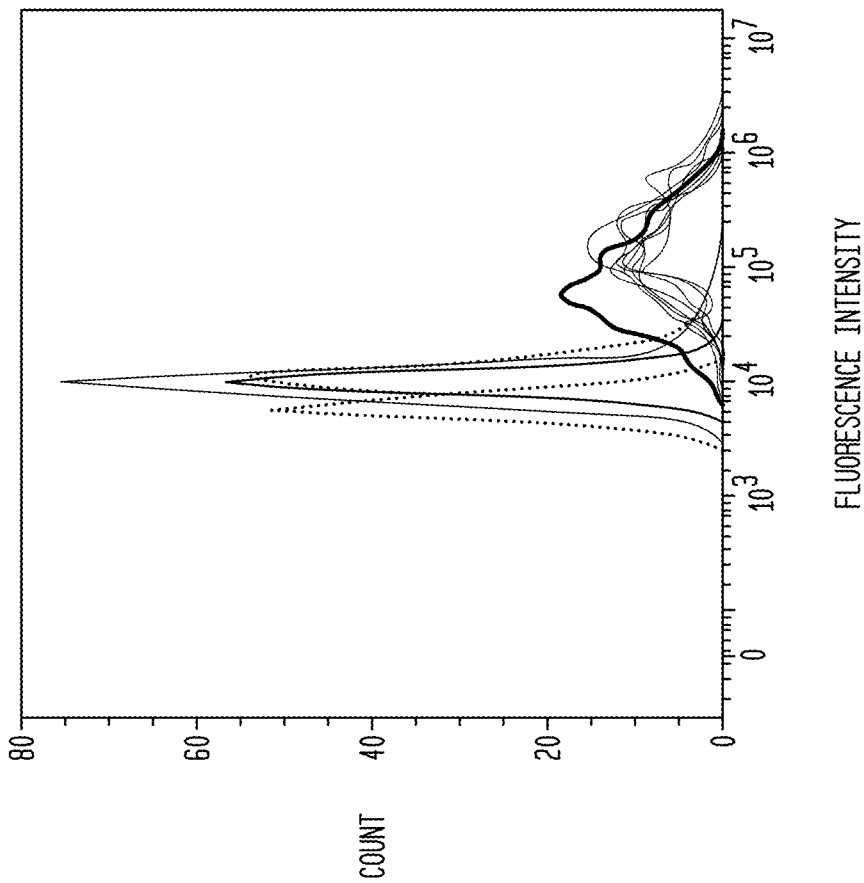
FIGS. 4A and 4B. Screening of purified monoclonal antibodies from expanded hybridomas.
Figure 5A:
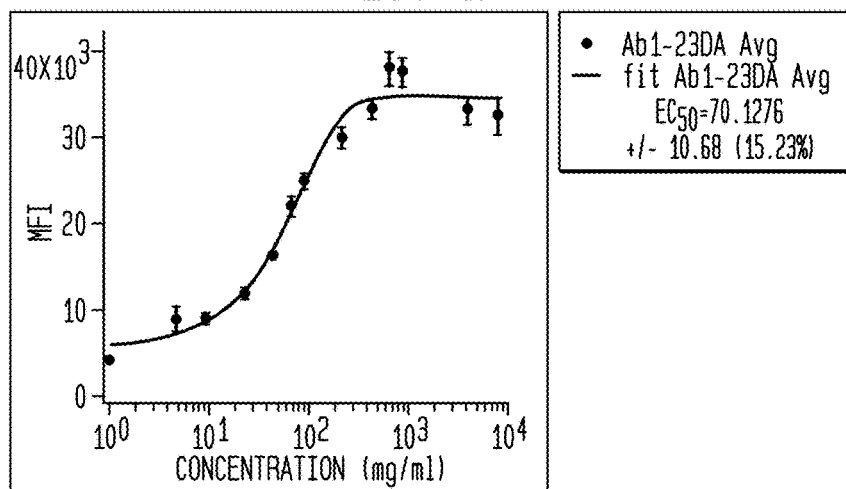
FIGS. 5A, 5B, 5C, 5D, and 5E. Affinity of anti-human FLT3/FLK2 antibodies determined by Effective Concentration (EC) curve using flow cytometry.
Figure 5B:
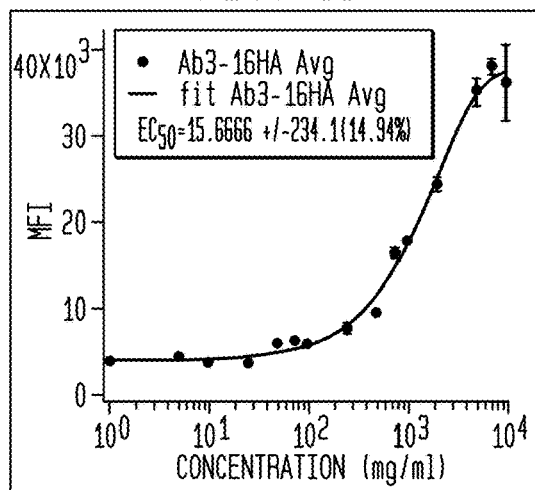
Figure 5D:
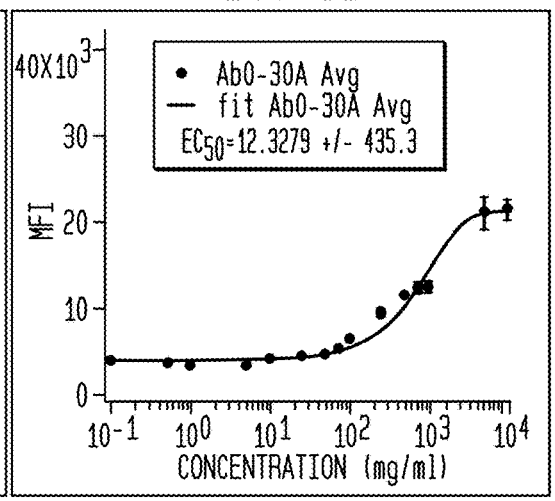
Figure 5C:
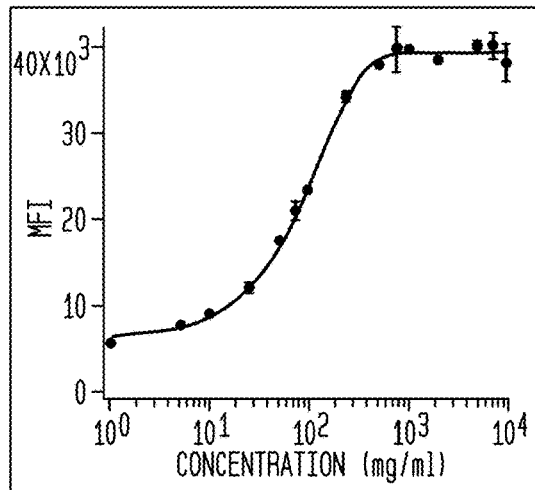
Figure 5E:
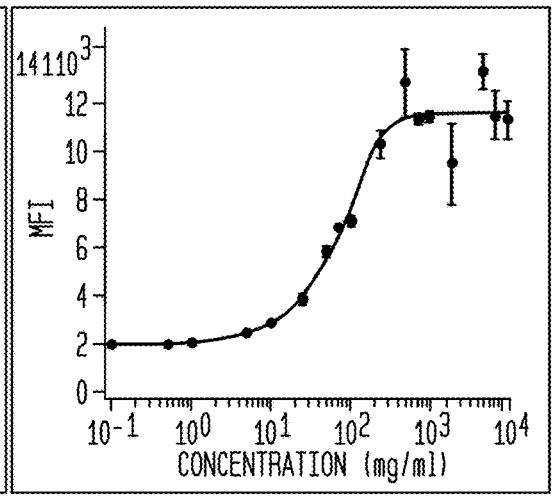

Approximately 3 weeks after the first immunization, spleens of immunized mice were collected and used for isolation of splenocytes. Isolated splenocytes we fused with SP2/0 cells and selected for the hybrid phenotype (hybridomas). Hybridomas were cultured in vitro and supernatants from the culture of the hybridomas were screened for the presence of anti-FLT3/FLK2 antibodies by flow cytometry (FIGS. 3A and 3B). Nine hybridoma clones demonstrated production of anti-FLT3/FLK2 antibodies. These hybridoma clones were expanded for isolation of monoclonal antibodies. The isolated monoclonal anti-FLT3/FLK2 antibodies were purified and tested for their selectivity (FIGS. 4A and 4B).

Example 4: Characterization of Specificity of Monoclonal Antibodies to the Human FLT3/FLK2 Receptor Protein Specificity of the monoclonal antibodies was determined by evaluating their affinity to the FLT3/FLK2 antigen. To define affinity of the anti-human FLT3/FLK2 antibodies, an Effective Concentration (EC) curve was built using flow cytometry. Nine monoclonal antibody clones were used to stain human REH cells that endogenously express human FLT3/FLK2. The concentration of the clones ranged from 1 ng/ml (6.25 pM) to 10,000 ng/ml (62.5 nM). Five clones with $EC_{50}$ ranging from around 70 ng/ml (437.5 pM) to 1566 ng/ml (9.79 nM) (FIGS. 5A, 5B, 5C, 5D, and 5E) were chosen for sequencing. Sequencing of the clones revealed that clones 1-23DA and 1-18 had the same amino acid sequences. The sequences of the clones are shown below.

```
MHC1692-1-23DA SEQUENCES:

Amino Acid Sequence in FASTA format (MHC1692LC.2\;M13F)-Light Chain
                                                              (SEQ ID NO: 5)
> MHC1692LC.2\;M13F
DIQMTQSPSSLSASLGERVSLTCRASQEISGYLSWLQQKPDGTIKRLIYAASTLHSGVPKRFSGSRSGSDYSLTISRLESEDVA
DYYCLQYASYPFTFGSGTKLEIR Nucleotide Sequence in FASTA format (MHC1692LC.2\;M13F)-Light Chain
                                                              (SEQ ID NO: 6)
> MHC1692LC.2\;M13F
GACATCCAGATGACCCAGTCTCCATCCTCCTTATCTGCCTCTCTGGGAGAAAGAGTCAGTCTCACTTGTCGGGCAAGTCAGGAA
```

-continued

ATTAGTGGTTACTTAAGCTGGCTTCAGCAGAAACCAGATGGAACTATTAAACGCCTGATCTACGCCGCATCCACTTTACATTCT
GGTGTCCCAAAAAGGTTCAGTGGCAGTAGGTCTGGGTCAGATTACTCTCTCACCATCAGCAGGCTTGAGTCTGAAGATGTTGCA
GACTATTACTGTCTACAATATGCTAGTTATCCATTCACGTTCGGCTCGGGGACAAAGTTGGAAATAAGA

Amino Acid Sequence in FASTA format (MHC1692HC.1\;M13F)-Heavy Chain
(SEQ ID NO: 7)
> MHC1692HC.1\;M13F
QVTLKESGPGILQPSQTLSLTCSFSGFSLSTSTMGVGWIRQPSGKGLEWLLHILWNDSKYYNPALKSRLTISKDTYNKQVFLKI
ANVDTADTATYYCARIVYYSTYVGYFDVWGAGTTVTVSS Nucleotide Sequence in FASTA format (MHC1692HC.1\;M13F)-Heavy Chain
(SEQ ID NO: 8)
> MHC1692HC.1\;M13F
CAGGTTACTCTGAAAGAGTCTGGCCCTGGGATATTGCAGCCCTCCCAGACCCTCAGTCTGACTTGTTCTTTCTCTGGGTTTTCT
CTGAGCACTTCTACTATGGGTGTAGGCTGGATTCGTCAGCCTTCAGGGAAGGGTCTGGAGTGGCTGTTACACATTTTGTGGAAT
GATAGTAAGTATTATAACCCAGCCCTGAAGAGCCGGCTCACAATCTCCAAGGATACCTACAACAAGCAGGTATTCCTCAAGATC
GCCAATGTGGACACTGCAGATACTGCCACATACTACTGTGCTCGAATAGTTTACTACTCTACCTACGTCGGGTACTTCGATGTC
TGGGGCGCAGGGACCACGGTCACCGTCTCCTCA

MHC1693-3-16HA SEQUENCES:

Amino Acid Sequence in FASTA format (MHC1693LC.1\;M13F)-Light Chain
(SEQ ID NO: 9)
> MHC1693LC.1\;M13F
DIVLTQSPASLAVSLGQRATISCRASESVDNYGISFMNWFQQKPGQSPKLLIYAVSNQGSGVPARFSGSGSGTDFSLNIHPMEE
DDTAMYFCQQSKEVPWTFGGGTKLEIK Nucleotide Sequence in FASTA format (MHC1693LC.1\;M13F)-Light Chain
(SEQ ID NO: 10)
> MHC1693LC.1\;M13F
GACATTGTGCTGACCCAATCTCCAGCTTCTTTGGCTGTGTCTCTAGGGCAGAGGGCCACCATCTCCTGCAGAGCCAGCGAAAGT
GTTGATAATTATGGCATTAGTTTTATGAACTGGTTCCAACAGAAACCAGGACAGTCACCCAAACTCCTCATCTATGCTGTATCC
AACCAAGGATCCGGGGTCCCTGCCAGGTTTAGTGGCAGTGGGTCTGGGACAGACTTCAGCCTCAACATCCATCCTATGGAGGAG
GATGATACTGCAATGTATTTCTGTCAGCAAAGTAAGGAGGTTCCGTGGACGTTCGGTGGAGGCACCAAGCTGGAAATCAAA Amino Acid Sequence in FASTA format (MHC1693HC.3\;M13F)-Heavy Chain
(SEQ ID NO: 11)
> MHC1693HC.3\;M13F
EVQLQQSGAELVRPGALVKLSCKGSGFNIKDYYIHWVKQRPEQGLEWIGRIDPENDITMYDPKFQGKASITADTSSNTAYLQLS
SLTSEDTAVYYCARNGNFFAYWGQGTLVTVSA Nucleotide Sequence in FASTA format (MHC1693HC.3\;M13F)-Heavy Chain
(SEQ ID NO: 12)
> MHC1693HC.3\;M13F
GAGGTTCAGCTGCAGCAGTCTGGGGCTGAGCTTGTGAGGCCAGGGGCCTTAGTCAAGTTGTCCTGCAAAGGTTCTGGCTTCAAC
ATTAAAGACTACTATATACACTGGGTGAAGCAGAGGCCTGAACAGGGCCTGGAGTGGATTGGAAGGATTGATCCTGAGAATGAT
ATTACTATGTATGACCCGAAGTTCCAGGGCAAGGCCAGTATAACAGCAGACACATCCTCCAACACAGCCTACCTGCAGCTCAGC
AGCCTGACATCTGAGGACACTGCCGTCTATTACTGTGCTAGAAATGGTAATTTCTTTGCTTACTGGGGCCAAGGGACTCTGGTC
ACTGTCTCTGCA

MHC1695-3-30A SEQUENCES:

Amino Acid Sequence in FASTA format (MHC1695LC.8\;M13F)-Light Chain
(SEQ ID NO: 13)
> MHC1695LC.8\;M13F
DIQMTQSPSSLSASLGERVSLTCRASQEISGYLSWLQQKPDGTIKRLIYAASTLNSGVPRRFSGSRSGSDYSLTISSLESEDFA
DYYCLQYASYPFTFGSGTKLEIK Nucleotide Sequence in FASTA format (MHC1695LC.8\;M13F)-Light Chain
(SEQ ID NO: 14)
> MHC1695LC.8\;M13F
GACATCCAGATGACCCAGTCTCCATCCTCCTTATCTGCCTCTCTGGGAGAAAGAGTCAGTCTCACTTGTCGGGCAAGTCAGGAA
ATTAGTGGTTACTTAAGCTGGCTTCAGCAGAAACCAGATGGAACTATTAAACGCCTGATCTACGCCGCATCCACTTTAAATTCT
GGTGTCCCAAGAAGGTTCAGTGGCAGTAGGTCTGGGTCAGATTATTCTCTCACCATCAGCAGCCTTGAGTCTGAAGATTTTGCA
GACTATTACTGTCTACAATATGCTAGTTATCCATTCACGTTCGGCTCGGGGACAAAGTTGGAAATAAAA Amino Acid Sequence in FASTA format (MHC1695HC.3\;M13F)-Heavy Chain
(SEQ ID NO: 15)
> MHC1695HC.3\;M13F
QVTLKESGPGILQPSQTLSLTCSFSGFSLSTSHMGVGWIRQPSGKGLEWLLHILWNDSVYYNPALKSRLTISKDTYNKQVFLKI
ANVDTADTATYYCARIVYYGISYVGYFDVWGAGTTVTVSS Nucleotide Sequence in FASTA format (MHC1695HC.3\;M13F)-Heavy Chain
(SEQ ID NO: 16)
> MHC1695HC.3\;M13F
CAGGTTACTCTGAAAGAGTCTGGCCCTGGGATATTGCAGCCCTCCCAGACCCTCAGTCTGACTTGTTCTTTCTCTGGGTTTTCA
CTGAGCACTTCTCACATGGGTGTAGGCTGGATTCGTCAGCCTTCAGGGAAGGGTCTGGAGTGGCTGTTACACATTTTGTGGAAT
GATAGTGTGTACTATAACCCAGCCCTGAAGAGCCGGCTCACAATCTCCAAGGATACCTACAACAAGCAGGTATTCCTCAAGATC
GCCAATGTGGACACTGCAGATACTGCCACATACTACTGTGCTCGAATAGTTTACTACGGTATTAGTTACGTCGGGTACTTCGAT
GTCTGGGGCGCAGGGACCACGGTCACCGTCTCCTCA

MHC1696-2-8IA SEQUENCES:

Amino Acid Sequence in FASTA format (MHC1696LC.3\;M13F)-Light Chain
(SEQ ID NO: 17)

> MHC1696LC.3\;M13F
DTVLTQSPATLSVTPGDSVSLSCRASQSISNNLHWYQQKSHESPRLLIKYGFQSISGIPSRFSGSGSGTDFTLRINSVETEDFG
MYFCQQTNSWPLTFGAGTKLELK

Nucleotide Sequence in FASTA format (MHC1696LC.3\;M13F)-Light Chain
(SEQ ID NO: 18)

> MHC1696LC.3\;M13F
GATACTGTGCTAACTCAATCTCCAGCCACCCTGTCTGTGACTCCAGGAGATAGCGTCAGTCTTTCCTGCAGGGCCAGCCAAAGT
ATTAGCAACAACCTACACTGGTATCAACAAAAATCACATGAGTCTCCAAGGCTTCTCATCAAGTATGGTTTCCAGTCCATCTCT
GGGATCCCCTCCAGGTTCAGTGGCAGTGGATCAGGGACAGATTTCACTCTCAGAATCAACAGTGTGGAGACTGAAGATTTTGGA
ATGTATTTCTGTCAACAGACTAACAGCTGGCCGCTCACGTTCGGTGCTGGGACCAAGCTGGAGCTGAAA

Amino Acid Sequence in FASTA format (MHC1696HC.2\;M13F)-Heavy Chain
(SEQ ID NO: 19)

> MHC1696HC.2\;M13F
EIQLQQSGPELVKPGASVKVSCKASGYSFIDYNMYWVKQSHGKSLEWIGYINPYNGGTSNNQKFKDKATLTVDKSSSTAFMHLN
SLTSEDSAVYYCARGTTGDYWGQGTTLTVSS

Nucleotide Sequence in FASTA format (MHC1696HC.2\;M13F)-Heavy Chain
(SEQ ID NO: 20)

> MHC1696HC.2\;M13F
GAGATCCAGCTGCAGCAGTCTGGACCTGAACTGGTGAAGCCTGGGGCTTCAGTGAAGGTATCCTGCAAGGCTTCTGGTTACTCA
TTCATTGACTACAACATGTACTGGGTGAAGCAGAGCCATGGAAAGAGCCTTGAGTGGATTGGATATATTAATCCTTACAATGGT
GGTACTAGCAACAACCAGAAGTTCAAGGACAAGGCCACATTGACTGTTGACAAGTCCTCCAGCACAGCCTTCATGCATCTCAAC
AGCCTGACATCTGAGGACTCTGCAGTCTATTACTGTGCAAGAGGTACTACGGGTGACTACTGGGGCCAAGGCACCACTCTCACA
GTCTCCTCA

MHC2279-1B11.E7 SEQUENCES:

Amino Acid Sequence in FASTA format (MHC2279LC.5\;M13F)-Light Chain
(SEQ ID NO: 21)

> MHC2279LC.5\;M13F
DIVLTQSPASLAVSLGQRATISCRASESVDNYGISFMNWFQQKPGQPPKLLIYAASNQGSGVPARFSGSGSGTDFSLNIHPMEE
DDTAMYFCQQSKEVPWTFGGGTKLEIK

Nucleotide Sequence in FASTA format (MHC2279LC.5\;M13F)-Light Chain
(SEQ ID NO: 22)

> MHC2279LC.5\;M13F
GACATTGTGCTGACCCAATCTCCAGCTTCTTTGGCTGTGTCTCTAGGGCAGAGGGCCACCATCTCCTGCAGAGCCAGCGAAAGT
GTTGATAATTATGGCATTAGTTTTATGAACTGGTTCCAACAGAAACCAGGACAGCCACCCAAACTCCTCATCTATGCTGCATCC
AACCAAGGATCCGGGGTCCCTGCCAGGTTTAGTGGCAGTGGGTCTGGGACAGACTTCAGCCTCAACATCCATCCTATGGAGGAG
GATGATACTGCAATGTATTTCTGTCAGCAAAGTAAGGAGGTTCCGTGGACGTTCGGTGGAGGCACCAAGCTGGAAATCAAA

Amino Acid Sequence in FASTA format (MHC2279HC.1\;M13F)-Heavy Chain
(SEQ ID NO: 23)

> MHC2279HC.1\;M13F
QVQLQQPGAELVMPGASVKLSCKASGYTFTSYWMHWVKQRPGQGLEWIGEIDPSDSYTNYNQKFKGKATLTVDKSSSTAYMQLS
SLTSEDSAVYYCARSAYYSKRDDYWGQGTTLTVSS

Nucleotide Sequence in FASTA format (MHC2279HC.1\;M13F)-Heavy Chain
(SEQ ID NO: 24)

> MHC2279HC.1\;M13F
CAGGTCCAACTGCAGCAGCCTGGGGCTGAGCTTGTGATGCCTGGGGCTTCAGTGAAGCTGTCCTGCAAGGCTTCTGGCTACACC
TTCACCAGCTACTGGATGCACTGGGTGAAGCAGAGGCCTGGACAAGGCCTTGAGTGGATCGGAGAGATTGATCCTTCTGATAGT
TATACTAACTACAATCAAAAGTTCAAGGGCAAGGCCACATTGACTGTAGACAAATCCTCCAGCACAGCCTACATGCAGCTCAGC
AGCCTGACATCTGAGGACTCTGCGGTCTATTACTGTGCAAGATCAGCCTACTATAGTAAAAGGGATGACTACTGGGGCCAAGGC
ACCACTCTCACAGTCTCCTCA

MHC1694-1-18BA SEQUENCES:

Amino Acid Sequence in FASTA format (MHC1694LC.2\;M13F)-Light Chain
(SEQ ID NO: 25)

> MHC1694LC.2\;M13F
DIQMTQSPSSLSASLGERVSLTCRASQEISGYLSWLQQKPDGTIKRLIYAASTLHSGVPKRFSGSRSGSDYSLTISRLESEDVA
DYYCLQYASYPFTFGSGTKLEIR

Nucleotide Sequence in FASTA format (MHC1694LC.2\;M13F)-Light Chain
(SEQ ID NO: 26)

> MHC1694LC.2\;M13F
GACATCCAGATGACCCAGTCTCCATCCTCCTTATCTGCCTCTCTGGGAGAAAGAGTCAGTCTCACTTGTCGGGCAAGTCAGGAA
ATTAGTGGTTACTTAAGCTGGCTTCAGCAGAAACCAGATGGAACTATTAAAGCGCCTGATCTACGCCGCATCCACTTTACATTCT
GGTGTCCCAAAAAGGTTCAGTGGCAGTAGGTCTGGGTCAGATTACTCTCTCACCATCAGCAGGCTTGAGTCTGAAGATGTTGCA
GACTATTACTGTCTACAATATGCTAGTTATCCATTCACGTTCGGCTCGGGGACAAAGTTGGAAATAAGA

Amino Acid Sequence in FASTA format (MHC1694HC.1\;M13F)-Heavy Chain (SEQ ID NO: 27)

```
> MHC1694HC.1\;M13F
QVTLKESGPGILQPSQTLSLTCSFSGFSLSTSTMGVGWIRQPSGKGLEWLLHILWNDSKYYNPALKSRLTISKDTYNKQVFLKI
ANVDTADTATYYCARIVYYSTYVGYFDVWGAGTTVTVSS
```

Nucleotide Sequence in FASTA format (MHC1694HC.1\;M13F)-Heavy Chain (SEQ ID NO: 28)

```
> MHC1694HC.1\;M13F
CAGGTTACTCTGAAAGAGTCTGGCCCTGGGATATTGCAGCCCTCCCAGACCCTCAGTCTGACTTGTTCTTTCTCTGGGTTTCT
CTGAGCACTTCTACTATGGGTGTAGGCTGGATTCGTCAGCCTTCAGGGAAGGGTCTGGAGTGGCTGTTACACATTTTGTGGAAT
GATAGTAAGTATTATAACCCAGCCCTGAAGAGCCGGCTCACAATCTCCAAGGATACCTACAACAAGCAGGTATTCCTCAAGATC
GCCAATGTGGACACTGCAGATACTGCCACATACTACTGTGCTCGAATAGTTTACTACTCTACCTACGTCGGGTACTTCGATGTC
TGGGGCGCAGGGACCACGGTCACCGTCTCCTCA
```

TABLE 6

| Sample ID | KD (M) | Kon (1/Ms) | Kdis (1/s) | Full X$^2$ | Full R$^{\wedge}2$ |
|---|---|---|---|---|---|
| MHC1694: 1-18BA | 5.76E$^{-12}$ | 2.46E$^{+06}$ | 1.42E$^{-05}$ | 0.0165 | 0.9962 |
| MHC2279: 1B11.E7 | 2.78E$^{-10}$ | 1.32E$^{+06}$ | 3.66E$^{-04}$ | 0.026 | 0.9777 |
| MHC1696: 2-8IA | 5.03E$^{-11}$ | 2.21E$^{+06}$ | 1.11E$^{-04}$ | 0.0216 | 0.9882 |

Example 5: Characterization of Internalization of Monoclonal Antibodies to the Human FLT3/FLK2 Receptor Protein Internalization of the monoclonal antibodies against FLT3/FLK2 (Example 3) was quantified by an internalization assay.

Briefly, 2× (4 µg/ml) working stocks of antibody were prepared on ice for antibodies 281A, 330A, 316HA and 123DA in staining buffer (1× phosphate buffered saline (PBS) with 2% bovine calf serum—BCS). A 4 µg/ml stock of anti-human CD135 (FLT3/FLK2) antibody (BioLegend #313302, Clone BV10A4H2) and a 4hig/ml isotype control (BioLegend #400102, Clone MOPC-21) were prepared as positive and negative CD135 staining controls, respectively. Reh cells, a human cell line that expresses CD135, were washed and re-suspended in staining buffer at a concentration of 2×10$^6$ cells/ml. Primary antibodies were added 1:1 with equal volume of cells for a final concentration of 2 µg/ml. Cells were stained in 15 mL centrifuge tubes for ease of washing. Next, cells were incubated on ice for 30 minutes, then washed three times in 5 ml of PBS to remove unbound primary antibodies. The stained cells were re-suspended in complete culture media (RPMI1640 containing glutamine and 2% BCS) and divided into parallel 96 well plates at 100 µl per well, with separate plates for each time point in triplicate wells. One set of plates was transferred to a 37° C. incubator, 5% CO$_2$, and a second set of plates was kept at 4° C. Incubation times were 10 minutes, 30 minutes, 1 hour, 2 hours, 3 hours and 4 hours. Following incubation, plates were washed in 1×PBS. Cells were then stained with an anti-mouse IgG Alexa 488 secondary antibody for 30 minutes on ice in the dark at a 1:800 dilution (Jackson Immuno #115545164). Triplicate control wells containing unstained cells and cells stained with secondary antibody alone were also prepared. After incubation with the secondary antibody, cells were washed a final time in 1×PBS containing 2% BCS and stained with 7AAD immediately prior to FACS.

Stained cells were analyzed by flow cytometry on a Beckman Coulter Cytoflex at a sample flow rate of 60 µl/minute. 10,000 events were captured for each well and FCS files were evaluated using FloJo software, Version 10. Mean fluorescent intensity (MFI) was calculated for the live cell population for Alexa 488 and the change in MFIs for each antibody were graphed versus time at 4° C. and 37° C.

Figure 6:
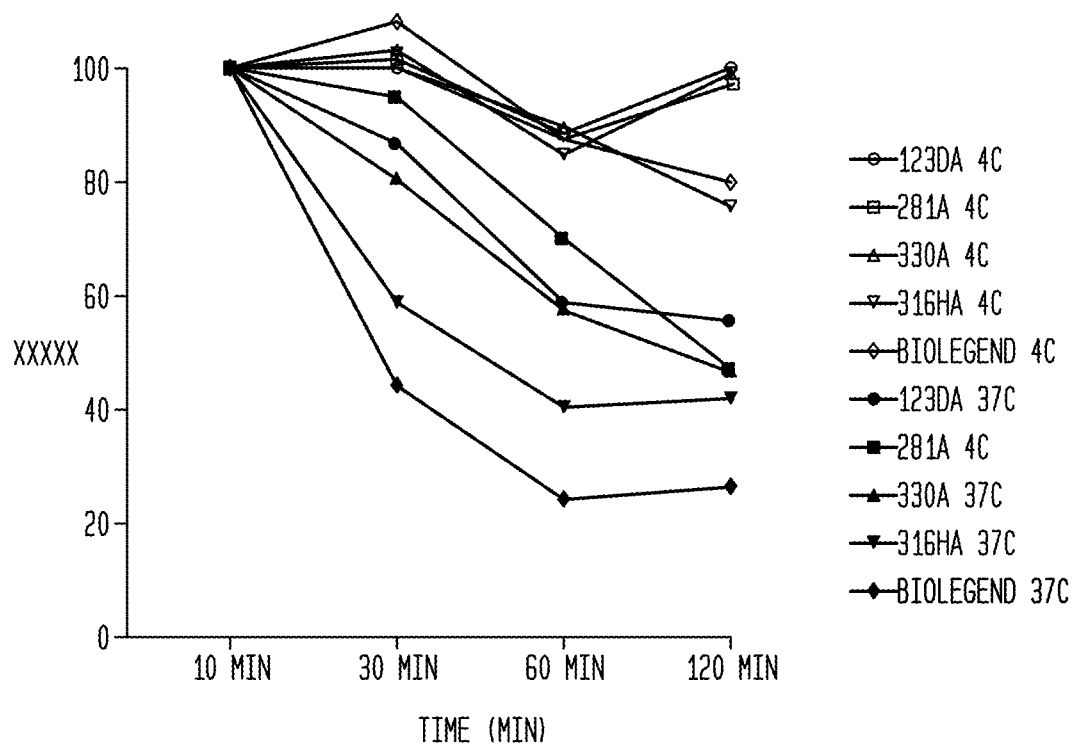
FIG. 6. Time Course of Anti-FLT3/FLK2 Antibody Internalization. Mean fluorescent intensity (MFI) of monoclonal mouse anti-human CD135 antibodies was detected with a secondary Alexa Fluor 488 plotted versus time for the live Reh cell population. Internalization assays were conducted at 37° C. in parallel with control cells that were kept on ice at 4° C. for 10, 30, 60 and 120 minutes. The percent change in MFI for each antibody (clones 123D, A281A, 330A and 316HA) was graphed versus time at 4° C. and 37° C. in triplicate over 2 hours, with MFI at 10 minutes set to 100%.

As shown in FIG. 6, all clones exhibited internalization, with clones 330A and 123DA displaying the most rapid internalization (FIG. 6). Without being limited by theory, it is hypothesized that the internalization property of anti-FLT3/FLK2 antibodies (clones 330A, 123DA, 316HA and 281A) render them effective as vehicles (e.g., Antibody-Drug-Conjugates—ADC) to deliver drugs/toxins inside targeted cells.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A monoclonal antibody or antigen binding fragment thereof, wherein an amino acid sequence of a light chain of an antigen-binding portion of the antibody or fragment thereof that binds to human FLT3/FLK2 receptor protein is selected from the group consisting of SEQ ID NO: 5, SEQ ID NO: 9, SEQ ID NO: 13, SEQ ID NO: 17, SEQ ID NO: 21, and SEQ ID NO: 25, and an amino acid sequence of a heavy chain of the antigen-binding portion of the antibody or fragment thereof that binds to human FLT3/FLK2 receptor protein is selected from the group consisting of SEQ ID NO: 7, SEQ ID NO: 11, SEQ ID NO: 15, SEQ ID NO: 19, SEQ ID NO: 23, and SEQ ID NO: 27.

2. The monoclonal antibody or antigen binding fragment thereof according to claim 1, wherein the amino acid sequence of a light chain of an antigen-binding portion of the antibody or fragment thereof that binds to human FLT3/FLK2 receptor protein is SEQ ID NO: 5 and the amino acid sequence of a heavy chain of the antigen-binding portion of the antibody or fragment thereof that binds to human FLT3/FLK2 receptor protein is SEQ ID NO: 7.

3. The monoclonal antibody or antigen binding fragment thereof according to claim 2, wherein a half maximal effective concentration (EC50) of the antibody or antigen-binding fragment thereof is between 1 ng/mL (6.25 pM) and 2,000 ng/mL (12.5 nM).

4. The monoclonal antibody or antigen binding fragment thereof according to claim 3, wherein the half maximal effective concentration (EC50) of the antibody or antigen-binding fragment thereof is between 10 ng/mL (62.5 pM) and 200 ng/mL (1.25 nM).

5. The monoclonal antibody or antigen binding fragment thereof according to claim 2, wherein binding of the antibody or antigen binding fragment thereof to human FLT3/FLK2 receptor protein on a cell is effective for the cell to internalize the bound antibody or antigen-binding fragment.

6. The monoclonal antibody or antigen binding fragment thereof according to claim 1, wherein the amino acid sequence of a light chain of an antigen-binding portion of the antibody or fragment thereof that binds to human FLT3/FLK2 receptor protein is SEQ ID NO: 9 and the amino acid sequence of a heavy chain of the antigen-binding portion of the antibody or fragment thereof that binds to human FLT3/FLK2 receptor protein is SEQ ID NO: 11.

7. The monoclonal antibody or antigen binding fragment thereof according to claim 6, wherein a half maximal effective concentration ($EC_{50}$) of the antibody or fragment thereof is between 1 ng/mL (6.25 pM) and 2,000 ng/mL (12.5 nM).

8. The monoclonal antibody or antigen binding fragment thereof according to claim 7, wherein the half maximal effective concentration ($EC_{50}$) of the antibody or antigen-binding fragment thereof is between 10 ng/mL (62.5 pM) and 200 ng/mL (1.25 nM).

9. The monoclonal antibody or antigen binding fragment thereof according to claim 6, wherein binding of the antibody or antigen binding fragment thereof to human FLT3/FLK2 receptor protein on a cell is effective for the cell to internalize the bound antibody or antigen-binding fragment.

10. The monoclonal antibody or antigen binding fragment thereof according to claim 1, wherein the amino acid sequence of a light chain of an antigen-binding portion of the antibody or fragment thereof that binds to human FLT3/FLK2 receptor protein is SEQ ID NO: 13 and the amino acid sequence of a heavy chain of the antigen-binding portion of the antibody or fragment thereof that binds to human FLT3/FLK2 receptor protein is SEQ ID NO: 15.

11. The monoclonal antibody or antigen binding fragment thereof according to claim 10, wherein a half maximal effective concentration ($EC_{50}$) of the antibody or antigen-binding fragment thereof is between 1 ng/mL (6.25 pM) and 2,000 ng/mL (12.5 nM).

12. The monoclonal antibody or antigen binding fragment thereof according to claim 11, wherein the half maximal effective concentration ($EC_{50}$) of the antibody or antigen-binding fragment thereof is between 10 ng/mL (62.5 pM) and 200 ng/mL (1.25 nM).

13. The monoclonal antibody or antigen binding fragment thereof according to claim 11, wherein binding of the antibody or antigen binding fragment thereof to human FLT3/FLK2 receptor protein on a cell is effective for the cell to internalize the bound antibody or antigen-binding fragment.

14. The monoclonal antibody or antigen binding fragment thereof according to claim 1, wherein the amino acid sequence of a light chain of an antigen-binding portion of the antibody or fragment thereof that binds to human FLT3/FLK2 receptor protein is SEQ ID NO: 17 and the amino acid sequence of a heavy chain of the antigen-binding portion of the antibody or fragment thereof that binds to human FLT3/FLK2 receptor protein is SEQ ID NO: 19.

15. The monoclonal antibody or antigen binding fragment thereof according to claim 14, wherein a half maximal effective concentration ($EC_{50}$) of the antibody or antigen-binding fragment thereof is between 1 ng/mL (6.25 pM) and 2,000 ng/mL (12.5 nM).

16. The monoclonal antibody or antigen binding fragment thereof according to claim 15, wherein the half maximal effective concentration ($EC_{50}$) of the antibody or antigen-binding fragment thereof is between 10 ng/mL (62.5 pM) and 200 ng/mL (1.25 nM).

17. The monoclonal antibody or antigen binding fragment thereof according to claim 14, wherein binding of the antibody or antigen binding fragment thereof to human FLT3/FLK2 receptor protein on a cell is effective for the cell to internalize the bound antibody or antigen-binding fragment.

18. A monoclonal antibody or antigen binding fragment thereof, wherein the amino acid sequence of a light chain of an antigen-binding portion of the antibody or fragment thereof that binds to human FLT3/FLK2 receptor protein is SEQ ID NO: 21 and the amino acid sequence of a heavy chain of the antigen-binding portion of the antibody or fragment thereof that binds to human FLT3/FLK2 receptor protein is SEQ ID NO: 23, wherein the monoclonal antibody or antigen binding fragment thereof does not compete with FLT3 ligand (FLT3L) when bound to FLT3/FLK2.

19. The monoclonal antibody or antigen binding fragment thereof according to claim 18, wherein a half maximal effective concentration ($EC_{50}$) of the antibody or fragment thereof is between 1 ng/mL (6.25 pM) and 2,000 ng/mL (12.5 nM).

20. The monoclonal antibody or antigen binding fragment thereof according to claim 19, wherein the half maximal effective concentration ($EC_{50}$) of the antibody or antigen-binding fragment thereof is between 10 ng/mL (62.5 pM) and 200 ng/mL (1.25 nM).

21. The monoclonal antibody or antigen binding fragment thereof according to claim 18, wherein binding of the antibody or antigen binding fragment thereof to human FLT3/FLK2 receptor protein on a cell is effective for the cell to internalize the bound antibody or antigen-binding fragment.

22. A monoclonal antibody or antigen binding fragment thereof, wherein the amino acid sequence of a light chain of an antigen-binding portion of the antibody or fragment thereof that binds to human FLT3/FLK2 receptor protein is SEQ ID NO: 25 and the amino acid sequence of a heavy chain of the antigen-binding portion of the antibody or fragment thereof that binds to human FLT3/FLK2 receptor protein is SEQ ID NO: 27, wherein the monoclonal antibody or antigen binding fragment thereof does not compete with FLT3 ligand (FLT3L) when bound to FLT3/FLK2.

23. The monoclonal antibody or antigen binding fragment thereof according to claim 22, wherein a half maximal effective concentration ($EC_{50}$) of the antibody or fragment thereof is between 1 ng/mL (6.25 pM) and 2,000 ng/mL (12.5 nM).

24. The monoclonal antibody or antigen binding fragment thereof according to claim 23, wherein the half maximal effective concentration ($EC_{50}$) of the antibody or antigen-binding fragment thereof is between 10 ng/mL (62.5 pM) and 200 ng/mL (1.25 nM).

25. The monoclonal antibody or antigen binding fragment thereof according to claim 22, wherein binding of the antibody or antigen binding fragment thereof to human FLT3/FLK2 receptor protein on a cell is effective for the cell to internalize the bound antibody or antigen-binding fragment.

* * * * *